(12) United States Patent
Takahashi

(10) Patent No.: US 9,334,302 B2
(45) Date of Patent: May 10, 2016

(54) METHOD FOR REMOVING FMOC GROUP

(71) Applicant: Ajinomoto Co., Inc., Chuo-ku (JP)

(72) Inventor: Daisuke Takahashi, Yokkaichi (JP)

(73) Assignee: AJINOMOTO CO., INC., Chuo-ku (JP)

( * ) Notice: Subject to any disclaimer, the term of this patent is extended or adjusted under 35 U.S.C. 154(b) by 0 days.

(21) Appl. No.: 14/305,841

(22) Filed: Jun. 16, 2014

(65) Prior Publication Data

US 2014/0296483 A1  Oct. 2, 2014

Related U.S. Application Data

(63) Continuation of application No. PCT/JP2012/082554, filed on Dec. 14, 2014.

(30) Foreign Application Priority Data

Dec. 15, 2011  (JP) .................. 2011/274901

(51) Int. Cl.
| | | |
|---|---|---|
| A61K 38/04 | (2006.01) | |
| C07K 5/00 | (2006.01) | |
| C07K 7/00 | (2006.01) | |
| C07K 16/00 | (2006.01) | |
| C07K 17/00 | (2006.01) | |
| C07K 1/00 | (2006.01) | |
| C07K 1/06 | (2006.01) | |
| C07C 227/16 | (2006.01) | |
| C07K 1/08 | (2006.01) | |
| C07B 43/04 | (2006.01) | |

(52) U.S. Cl.
CPC ............... C07K 1/00 (2013.01); C07C 227/16 (2013.01); C07K 1/063 (2013.01); C07K 1/064 (2013.01); C07K 1/08 (2013.01); C07B 43/04 (2013.01)

(58) Field of Classification Search
CPC ............ C07K 7/06; C07K 7/08; C07K 14/00; C07K 16/00; C07K 1/02; C07K 1/06; C07K 2/00; C07K 7/00; C07K 17/00
See application file for complete search history.

(56) References Cited

U.S. PATENT DOCUMENTS

| 7,435,791 B2 | 10/2008 | Eggen et al. | |
|---|---|---|---|
| 2002/0058788 A1* | 5/2002 | Sheppeck, II | ................ 530/335 |
| 2003/0018164 A1 | 1/2003 | Eggen et al. | |
| 2004/0082760 A1 | 4/2004 | Eggen et al. | |
| 2004/0087768 A1 | 5/2004 | Eggen et al. | |
| 2006/0063918 A1 | 3/2006 | Eggen et al. | |
| 2010/0184952 A1 | 7/2010 | Takahashi | |
| 2011/0190475 A1 | 8/2011 | Nishiuchi et al. | |

FOREIGN PATENT DOCUMENTS

| JP | 2003-055396 A | 2/2003 |
|---|---|---|
| JP | 2008-303195 A | 12/2008 |
| WO | WO 2009/014177 A1 | 1/2009 |
| WO | WO 2010/016551 A | 2/2010 |

OTHER PUBLICATIONS

Katritzky et al., Org. Biomol. Chem., 2011, 9, 596-599.*
Experiment 3, Extraction Separation of an Acidic, a Basic and a Neutral, available online at: https://web.archive.org/web/20100331115548/http://www.bc.edu/schools/cas/chemistry/undergrad/org/fall/Extract.pdf, archived on 2010.*
International Search Report issued Mar. 12, 2013 in PCT/JP2012/082554.
Jikken Kagaku Kouza fifth edition, "The fifth series of experimental chemistry", Maruzen Co., Ltd., vol. 16, Mar. 31, 2005, p. 272 and Cover Pages (written in Japanese).
James E. Sheppeck II, et al, "A convenient and scaleable procedure for removing the Fmoc group in solution" Tetrahedron Letters, vol. 41, No. 28, 2000, pp. 5329-5333.

* cited by examiner

*Primary Examiner* — James H Alstrum Acevedo
*Assistant Examiner* — Kaipeen Yang
(74) *Attorney, Agent, or Firm* — Oblon, McClelland, Maier & Neustadt, L.L.P.

(57) ABSTRACT

The present invention relates to a method of removing an Fmoc group, including a step of mixing a compound represented by the formula (I):

$$HS-L-COOH \qquad (I)$$

wherein L is a $C_{1-8}$ alkylene group optionally having substituent(s), an amino group-containing compound protected by an Fmoc group, and a base to give a reaction mixture containing a compound represented by the formula (II):

$$Fm-S-L-COOH \qquad (II)$$

wherein Fm is a 9-fluorenylmethyl group, and L is as mentioned above, and an amino group-containing compound, and a step of removing the compound represented by the formula (II) by washing the obtained reaction mixture with a basic aqueous solution. According to the present invention, a removal method of Fmoc group, which can remove a dibenzofulvene derivative as a byproduct with ease, can be provided.

18 Claims, No Drawings

METHOD FOR REMOVING FMOC GROUP

CROSS REFERENCES TO RELATED APPLICATIONS

This application is a continuation of International Patent Application No. PCT/JP2012/082554, filed on Dec. 14, 2012, and claims priority to Japanese Patent Application No. 2011-274901, filed on Dec. 15, 2011, both of which are incorporated herein by reference in their entireties.

BACKGROUND OF THE INVENTION

1. Field of the Invention

The present invention relates to a method of removing an Fmoc (9-fluorenylmethoxycarbonyl) group, and a production method of a peptide by using said method.

2. Discussion of the Background

Fmoc group is an important protecting group of amino acid and an amino group of a peptide in the peptide synthesis. As a result of this removal of the Fmoc group, dibenzofulvene (DBF) or DBF derivative is produced as a byproduct. Fmoc group is generally removed by using a base. For example, when Fmoc group is removed by using an amine, an adduct of DBF and amine (hereinafter sometimes to be abbreviated as a "DBF-amine adduct") is by-produced as a DBF derivative. When the peptide synthesis is continued while DBF or DBF derivative still remains, a side reaction such as 9-fluorenylmethylation occurs. Thus, it is desirable to remove DBF or DBF derivative efficiently. In addition, when amine is used to remove Fmoc group and DBF in the peptide synthesis, the amine needs to be removed before the next condensation step.

Non-patent document 1 describes a method for removal of a DBF-amine adduct in the liquid phase peptide synthesis, which includes adding a hydrocarbon solvent such as hexane and the like for trituration of a residue obtained by concentrating a reaction extract to dryness, thereby dissolving a DBF-amine adduct in the solvent, and isolating the deprotected peptide as crystals. However, this method is poor in operability, sometimes fails to reproduce at a large scale, and is unsuitable for industrial production. In addition, when a desired deprotected peptide is an oily substance, this method cannot be used. Furthermore, the method is associated with problems of low recovery rate and the like due to dissolution of peptide itself in a hydrocarbon solvent when the peptide chain is short.

To solve the problem mentioned above, patent document 1 describes a method including stirring a reaction mixture after removal of the Fmoc group in a hydrocarbon solvent and a polar organic solvent, separating the hydrocarbon solvent layer and the polar organic solvent layer, and removing the hydrocarbon solvent layer in which a DBF and/or DBF-amine adduct is dissolved. Patent document 2 describes a method including contacting a reaction mixture containing a DBF-amine adduct with carbon dioxide to form a carbonate of a DBF-amine adduct, and removing the carbonate. However, both patent documents 1 and 2 do not describe use of sulfanyl group (SH)-containing fatty acid for the removal of an Fmoc group.

On the other hand, non-patent document 2 describes a method including using 1-octanethiol and the like as scavengers of DBF produced during removal of Fmoc group. In this method, an adduct of DBF and thiol (hereinafter sometimes to be abbreviated as a "DBF-thiol adduct") is produced. In an experiment using 1-octanethiol in non-patent document 2, (a) trituration or (b) trituration and recrystallization was performed in the same manner as in the method of non-patent document 1 to remove a byproduced DBF-thiol adduct (Table 1), and the operability is poor.

Patent document 3 describes a method including using an amine containing free anion or potential anion, or a thiol containing free anion or potential anion, as a scavenger to remove a residual carboxy component in the peptide synthesis comprising reacting an excess amount of the carboxy component with an amino component. Patent document 3 further describes, "the aforementioned scavengers are also used for the deprotection of a peptide under elongation". However, in the method of patent document 3, the aforementioned scavengers (thiol containing free anion or potential anion etc.) are used to deprotect peptide to perform removal of a temporal protecting group contained in the free anion (scavenger), and deprotection of the N-terminal of peptide under elongation by a single treatment. Patent document 3 does not describe use of the aforementioned scavengers for removing Fmoc group or trapping DBF.

Patent document 4 describes a method of producing a compound represented by Fm—S—X—COOH (wherein Fm is 9-fluorenylmethyl), comprising reacting a compound represented by HS—X—COOH (wherein X is an alkylene chain having 1-5 carbon atoms) with a compound represented by Fm—$R^1$ (wherein Fm is 9-fluorenylmethyl, and $R^1$ is a chlorine atom and the like), or Fmoc-$R^2$ (wherein Fmoc is 9-fluorenylmethoxycarbonyl, and $R^2$ is succinimidyloxy and the like). However, patent document 4 relates to a production method of Fm—S—X—COOH, and does not relate to the deprotection of an amino group-containing compound protected by an Fmoc group. Patent document 4 proposes using an inorganic base since the above-mentioned reaction using an organic base affords HS—X—COOH only in a low yield.

DOCUMENT LIST

Patent Documents patent document 1: WO 2009/014177
patent document 2: WO 2010/016551
patent document 3: JP-A-2003-55396
patent document 4: JP-A-2008-303195

Non-Patent Documents non-patent document 1: Jikken Kagaku Kouza fifth edition, Maruzen Co., Ltd, published on Mar. 31, 2005, vol. 16, page 272
non-patent document 2: James E. Sheppeck II et al., "A convenient and scaleable procedure for removing the Fmoc group in solution", Tetrahedron Letter 41 (2000) 5329-5333

SUMMARY OF THE INVENTION

Problems to be Solved by the Invention

The present invention has been made taking note of the above-mentioned situation, and aims to provide a method of removing an Fmoc group, which can easily remove a byproduct, a DBF derivative.

Means of Solving the Problems

As mentioned above, since an Fmoc group is removed from a protected amino group by using a base, those of ordinary skill in the art do not expect the presence of an acid in the removal reaction of an Fmoc group. Nevertheless, the present inventors have conducted intensive studies in an attempt to achieve the above-mentioned object and surprisingly found that, when removing an Fmoc group by using a base, the removal proceeds even in the presence of sulfanyl group-containing fatty acid, and a DBF derivative (i.e., DBF-sulfanyl group-containing fatty acid adduct) can be successfully removed by subsequently washing with a basic aqueous solution.

While non-patent document 2 suggests use of thiosalicylic acid as a scavenger of DBF, an experiment of thiosalicylic acid has not been performed, and thiosalicylic acid is a mere exemplification. When the present inventors performed an experiment using thiosalicylic acid, a DBF derivative (i.e., DBF-thiosalicylic acid adduct) was not sufficiently produced (the following Comparative Example 1). The present invention based on these findings is as described below.

[1] A method of removing an Fmoc group, comprising a step of mixing a compound represented by the formula (I):

$$\text{HS-L-COOH} \qquad (I)$$

wherein L is a $C_{1-8}$ alkylene group optionally having substituent(s), an amino group-containing compound protected by an Fmoc group, and a base to give a reaction mixture containing a compound represented by the formula (II):

$$\text{Fm—S-L-COOH} \qquad (II)$$

wherein Fm is a 9-fluorenylmethyl group, and L is as mentioned above, and an amino group-containing compound, and a step of removing the compound represented by the formula (II) by washing the obtained reaction mixture with a basic aqueous solution.

[2] The method of the above-mentioned [1], wherein the base is an organic base.

[3] The method of the above-mentioned [2], wherein the organic base is 1,8-diazabicyclo[5.4.0]-7-undecene.

[4] The method of any one of the above-mentioned [1]-[3], wherein the compound represented by the formula (I) is at least one selected from the group consisting of 3-mercaptopropionic acid, thiomalic acid and cysteine.

[5] The method of any one of the above-mentioned [1]-[4], wherein the basic aqueous solution is an aqueous solution of at least one selected from the group consisting of lithium carbonate, potassium carbonate, sodium carbonate, lithium hydrogen carbonate, potassium hydrogen carbonate, sodium hydrogen carbonate, lithium hydroxide, potassium hydroxide and sodium hydroxide.

[6] The method of any one of the above-mentioned [1]-[5], wherein the amino group-containing compound protected by an Fmoc group is N-Fmoc-C-protected peptide, N-Fmoc-C-protected amino acid or N-Fmoc-C-protected amino acid amide, and the obtained amino group-containing compound is C-protected peptide, C-protected amino acid or C-protected amino acid amide.

[7] A method of producing a peptide by a liquid phase synthesis method, comprising the method of the above-mentioned [6].

[8] The production method of the above-mentioned [7], comprising (1) a step of condensing C-protected peptide, C-protected amino acid or C-protected amino acid amide, and N-Fmoc amino acid or N-Fmoc peptide in the presence of a condensing agent to give an N-Fmoc-C-protected peptide, and/or (2) a step of condensing C-protected peptide, C-protected amino acid or C-protected amino acid amide, and N-Fmoc amino acid active ester or N-Fmoc peptide active ester to give an N-Fmoc-C-protected peptide.

[9] The production method of the above-mentioned [8], wherein the aforementioned step (1) is performed in the further presence of an activator.

[10] The production method of the above-mentioned [8] or [9], wherein the C-protected peptide, C-protected amino acid or C-protected amino acid amide obtained by the method of the above-mentioned [6] is used in the aforementioned step (1) and/or the aforementioned step (2) without isolating as a solid.

[11] The production method of the above-mentioned [10], wherein the peptide is produced by one-pot synthesis.

In the following, the "compound represented by the formula (I)" and the like are sometimes to be abbreviated as "compound (I)" and the like.

Effect of the Invention

According to the removal method of the Fmoc group of the present invention, DBF is trapped by compound (I), compound (II) as a byproduct can be easily removed by washing with a basic aqueous solution. The removal method of the Fmoc group of the present invention does not require complicated operations such as trituration and the like, and can also be applied easily to large-scale reactions. In addition, by applying the removal method of the Fmoc group of the present invention to the peptide synthesis, intermediate peptide obtained after deprotection of Fmoc can be used, without isolating as a solid, for the next condensation step, which enables one-pot synthesis of peptide and is particularly preferable for industrial production.

DETAILED DESCRIPTION OF THE PREFERRED EMBODIMENTS

1. Symbols

The meanings of the symbols used in the present invention (that is, DESCRIPTION and Claims) are described below.

Ac: acetyl
Alloc: allyloxycarbonyl
At: 7-azabenzotriazol-1-yl
Boc: tert-butoxycarbonyl
BOP: 1-benzotriazolyloxy-tris-dimethylamino-phosphonium hexafluorophosphate
Bpr: 1,1-dimethyl-2-phenyl-ethyl
Bsmoc: 1,1-dioxobenzo[b]thiophen-2-ylmethoxycarbonyl
Bt: benzotriazol-1-yl
Bzl: benzyl
Bzl(2,4-OPhy): 2,4-di(2',3'-dihydrophytyloxy)benzyl
Bzl(3,4,5-OPhy): 3,4,5-tri(2',3'-dihydrophytyloxy)benzyl
Bzl(2-OBzl(3,4,5-OPhy)-4-OMe): 2-[3,4,5-tri(2',3'-dihydrophytyloxy)benzyloxybenzyloxy]-4-methoxybenzyl
CDI: carbonyldiimidazole
6-Cl-HOBt(HOCt): 6-chloro-1-hydroxybenzotriazole
CPME: cyclopentyl methyl ether
Ct: 6-chlorobenzotriazol-1-yl
DABCO: 1,4-diazabicyclo[2.2.2]octane
DBF: dibenzofulvene
DBU: 1,8-diazabicyclo[5.4.0]-7-undecene
DCC: dicyclohexylcarbodiimide
Dhbt: 3,4-dihydro-4-oxo-1,2,3-benzotriazin-3-yl
DIPC: diisopropylcarbodiimide
DMAP: N,N-dimethyl-4-aminopyridine
Dmb: 2,4-dimethoxybenzyl
DMF: N,N-dimethylformamide
DMT-MM: 4-(4,6-dimethoxy-1,3,5-triazin-2-yl)-4-methylmorpholinium chloride Dpm: diphenylmethyl
Dpm(4,4'-OPhy): 4,4'-(2',3'-dihydrophytyloxy)diphenylmethyl
EDC: 1-ethyl-3-(3-dimethylaminopropyl)-carbodiimide
EDC.HCl: 1-ethyl-3-(3-dimethylaminopropyl)-carbodiimide hydrochloride
Et: ethyl
Fm: 9-fluorenylmethyl
Fmoc: 9-fluorenylmethoxycarbonyl
HATU: O-(7-azabenzotriazol-1-yl)-1,1,3,3-tetramethyluronium hexafluorophosphate
HBTU: O-(benzotriazol-1-yl)-1,1,3,3-tetramethyluronium hexafluorophosphate
HCTU: 0-(6-chlorobenzotriazol-1-yl)-1,1,3,3-tetramethyluronium hexafluorophosphate
HOAt: 1-hydroxy-7-azabenzotriazole
HOBt: 1-hydroxybenzotriazole
HONb: N-hydroxy-5-norbornane-2,3-dicarboxyimide
HOOBt(HODhbt): 3-hydroxy-3,4-dihydro-4-oxo-1,2,3-benzotriazine
HOPht: N-hydroxyphthalimide
HOSu: N-hydroxysuccinimide
iPr: isopropyl
Me: methyl
MsOH: methanesulfonic acid
Nb: 5-norbornane-2,3-dicarboxyimidoyl
NMP: N-methylpyrrolidone
Pbf: 2,2,4,6,7-pentamethyldihydrobenzofuran-5-sulfonyl
Pht: phthalimidoyl
PyBOP: 1-benzotriazolyloxy-tris-pyrrolidino-phosphonium hexafluorophosphate
PyBroP: bromo-tris-pyrrolidino-phosphonium hexafluorophosphate
Su: succinimidoyl
TBTU: O-benzotriazol-1-yl-1,1,3,3-tetramethyluronium tetrafluoroborate
tBu: tert-butyl
Trt: trityl
THF: tetrahydrofuran
TsOH: p-toluenesulfonic acid
Z: benzyloxycarbonyl
$AA_n$: amino acid residue (subscript n is any integer of 1 or more, and shows the order of $AA_n$ from peptide C-terminal)
$PG_0$: protecting group of C-terminal carboxyl group or C-terminal amide group of peptide
$PG_n$: amino-protecting group (subscript n is any integer of 1 or more, and $PG_n$ is a protecting group of amino group for $AA_n$)
HOE: activator
E: activated group
Gly: glycine
Ala: alanine
Val: valine
Leu: leucine
Ile: isoleucine
Met: methionine
Phe: phenylalanine
Tyr: tyrosine
Trp: tryptophan
His: histidine
Lys: lysine
Arg: arginine
Ser: serine
Thr: threonine
Asp: aspartic acid
Glu: glutamic acid
Asn: asparagine
Gln: glutamine
Cys: cysteine
Pro: proline
Orn: ornithine
Sar: sarcosine
β-Ala: β-alanine
GABA: γ-aminobutyric acid
Dap: 2,3-diaminopropionic acid Examples of the protecting group of the C-terminal carboxy group for $PG_0$ include alkyl groups such as Me, Et, iPr, tBu and the like, Z, Fm, Trt, Dpm, Bpr, 1-1-dimethylbenzyl, dimethylphenyl and the like.

Examples of the protecting group of the C-terminal amide group for $PG_0$ include Dmb, bis(4-methoxyphenyl)methyl, trityl and the like. The amide group optionally has substituent(s) such as an alkyl group and the like. The amide group is also referred to as a carbamoyl group.

In addition, as the protecting group of the C-terminal carboxy group or C-terminal amide group for $PG_0$,
(1) a protecting group using the diphenylmethane compound described in WO 2010/113939A1 as a protecting reagent,
(2) a protecting group using the fluorene compound described in WO 2010/104169A1 as a protecting reagent,
(3) a protecting group using the benzyl compound described in WO 2011/078295A1 as a protecting reagent,
(4) a protecting group using the branched chain-containing aromatic compound described in WO 2012/029794A1 as a protecting reagent
and the like can be used.

When the C-terminal carboxy group or C-terminal amide group is protected using such protecting reagents, the liposolubility of the below-mentioned N-Fmoc-C-protected peptide and the like, and C-protected peptide and the like can be improved. In the production method of peptide by the below-mentioned liquid phase synthesis method, for example, impurities can be efficiently removed from the aqueous layer in washing with water in the workup of the coupling step.

Examples of the diphenylmethane compound described in WO 2010/113939A1 include
2,3,4-trioctadecanoxybenzohydrol;
[phenyl(2,3,4-trioctadecanoxyphenyl)methyl]amine;
4,4'-didocosoxybenzohydrol;
di(4-docosoxyphenyl)methylamine;
4,4-di(12-docosoxydodecyloxy)benzohydrol;
amino-bis[4-(12-docosoxydodecyloxy)phenyl]methane;
N-benzyl-[bis(4-docosyloxyphenyl)]methylamine;
(4-methoxy-phenyl)-[4-(3,4,5-tris-octadecyloxy-cyclohexylmethoxy)-phenyl]-methanol;
{(4-methoxy-phenyl)-[4-(3,4,5-tris-octadecyloxy-cyclohexylmethoxy)-phenyl]-methyl}-amine;
[bis-(4-docosoxy-phenyl)-methyl]-amine
and the like.

Examples of the fluorene compound described in WO 2010/104169A1 include
2-docosyloxy-9-(4-chlorophenyl)-9-fluorenol;
2-docosyloxy-9-(4-chlorophenyl)-9-bromofluorene;
2,7-didocosyloxy-9-(4-chlorophenyl)-9-bromofluorene;
2-(12-docosyloxy-dodecanoxy)-9-(3-fluorophenyl)-9-bromofluorene;
1,12-bis-[12-(2'-O-9-(4-chlorophenyl)-9-fluorenol)-dodecyloxy]-dodecane;
1,12-bis-[12-(2'-O-9-(4-chlorophenyl)-9-bromofluorene)-dodecyloxy]-dodecane;
2-(3-octadecyloxy-2,2-bis-octadecyloxymethyl-propoxy)-9-(4-chlorophenyl)-9-fluorenol;
2-(3-octadecyloxy-2,2-bis-octadecyloxymethyl-propoxy)-9-(4-chlorophenyl)-9-bromofluorene;

9-(4-chlorophenyl)-2-(3,4,5-tris(octadecyloxy)cyclohexyl-methoxy)-9-fluorenol;
9-(4-chlorophenyl)-2-(3,4,5-tris(octadecyloxy)cyclohexyl-methoxy)-9-bromofluorene
and the like.

Examples of the benzyl compound described in WO 2011/078295A1 include
4-(12'-docosyloxy-1'-dodecyloxy)benzyl alcohol;
4-(12'-docosyloxy-1'-dodecyloxy)-2-methoxybenzyl alcohol;
4-(12'-docosyloxy-1'-dodecyloxy)-2-methoxybenzylamine;
2-(12'-docosyloxy-1'-dodecyloxy)-4-methoxybenzyl alcohol;
2-(12'-docosyloxy-1'-dodecyloxy)-4-methoxybenzylamine;
4-methoxy-2-[3',4',5'-tris(octadecyloxy)benzyloxy]benzyl alcohol;
2-[3',5'-di(docosyloxy)benzyloxy]-4-methoxybenzyl alcohol;
2-methoxy-4-[2',2',2'-tris(octadecyloxymethyl)ethoxy]benzyl alcohol;
2-methoxy-4-[2',2',2'-tris(octadecyloxymethyl)ethoxy]benzylamine;
4-methoxy-2-[3',4',5'-tris(octadecyloxy)cyclohexylmethyloxy]benzyl alcohol;
4-[3',4',5'-tris(octadecyloxy)cyclohexylmethyloxy]benzyl alcohol;
1,22-bis[12-(4-hydroxymethyl-3-methoxyphenoxy)dodecyloxy]docosane;
1,22-bis[12-(2-hydroxymethyl-5-methoxyphenoxy)dodecyloxy]docosane;
2-docosyloxy-4-methoxybenzyl alcohol;
2-methoxy-4-[3',4',5'-tris(octadecyloxy)cyclohexylmethyloxy]benzyl alcohol;
3,5-dimethoxy-4-[3',4',5'-tris(octadecyloxy)cyclohexylmethyloxy]benzyl alcohol;
N-(4-hydroxymethyl-3-methoxyphenyl)-3,4,5-tris(octadecyloxy)cyclohexylcarboxamide;
N-(5-hydroxymethyl-2-methoxyphenyl)-3,4,5-tris(octadecyloxy)cyclohexylcarboxamide;
N-(4-hydroxymethylphenyl)-3,4,5-tris(octadecyloxy)cyclohexylcarboxamide
and the like.

Examples of the branched chain-containing aromatic compound described in WO 2012/029794A1 include
2,4-di(2',3'-dihydrophytyloxy)benzyl alcohol;
3,5-di(2',3'-dihydrophytyloxy)benzyl alcohol;
4-(2',3'-dihydrophytyloxy)benzyl alcohol;
1-[(2-chloro-5-(2',3'-dihydrophytyloxy)phenyl)]-1-phenylmethaneamine;
3,4,5-tri(2',3'-dihydrophytyloxy)benzyl alcohol;
3,4,5-tri(2',3'-dihydrophytyloxy)benzylamine;
4-(2',3'-dihydrophytyloxy)benzylamine;
2-[3',4',5'-tri(2",3"-dihydrophytyloxy)benzyloxy]-4-methoxybenzyl alcohol;
4-(2',3'-dihydrophytyloxy)-2-methoxybenzyl alcohol;
4-(2',3'-dihydrophytyloxy)-2-methoxybenzylamine;
4-(2',3'-dihydrophytyloxy)-2-methylbenzyl alcohol;
4-(2',3'-dihydrophytyloxy)-2-methylbenzylamine;
2,2,4,8,10,10-hexamethyl-5-dodecanoic acid (4-hydroxymethyl)phenylamide;
4-(3,7,11-trimethyldodecyloxy)benzyl alcohol;
2-(3,7,11-trimethyldodecyloxy)-9-phenylfluorene-9-ol
and the like.

Examples of the amino-protecting group for $PG_n$ include Boc, Z, Fmoc, Bsmoc, Alloc, Ac and the like.

The activated group for E means a group which can be easily dissociated as "EO$^-$" on nucleophilic attack by an amino group and produce an amide bond, and examples thereof include Bt, Ct, At, OBt, Su, Pht, Nb, pentafluorophenyl and the like.

2. Terms

The terms used in the present invention are sequentially explained below.

The "amino group-containing compound" in the present invention means a compound having the primary amino group and/or the secondary amino group.

The "amino group-containing compound protected by an Fmoc group" means a compound wherein at least one of the primary amino group and/or the secondary amino group that the amino group-containing compound has is protected by an Fmoc group.

When an amino acid is indicated as "H-AA-OH" in the present invention, it means that the left side is an amino group, the right side is a carboxy group, and both the amino group and the carboxy group are not protected.

An amino acid wherein the carboxy group is protected is indicated as "H-AA-OPG$_0$", and an amino acid wherein the amino group is protected is indicated as "PG$_n$-AA-OH".

An amino acid wherein the amino group is protected and the carboxy group is active-esterified is indicated as "PG$_n$-AA-OE".

A symmetric anhydride of PG$_n$-AA-OH is indicated as "(PG$_n$-AA)$_2$-O".

In the present invention, when amino acid amide is indicated as "H-AA-NH$_2$", it means that the left side is an amino group, the right side is an amide group, and both the amino group and the amide group are not protected.

An amino acid amide wherein the amide group is protected is indicated as "H-AA-NHPG$_0$", and an amino acid amide wherein the amino group is protected is indicated as "PG$_n$-AA-NH$_2$".

An amino acid or amino acid amide having a protected side chain functional group is indicated as "H-AA(PG)-(OH or NH$_2$)" (PG is a protecting group of the side chain functional group).

When peptide is indicated as "H-AA$_{n'}$-AA$_{n'-1}$-...-AA$_1$-(OH or NH$_2$)" (subscript n' is an integer of two or more) in the present invention, it means that the left side is the N-terminal, the right side is the C-terminal, and the peptide contains amino acid residues in the number of n' having unprotected N-terminal and unprotected C-terminal. Here, the N-terminal is not limited to an α-position amino group of the amino acid residue and, when peptide elongation is performed via this side chain amino group, it also includes the side chain amino group (e.g., an ε-amino group of Lys), hereinafter the same.

A peptide with protected C-terminal is indicated as "H-AA$_{n'}$-AA$_{n'-1}$-...-AA$_1$-(OPG$_0$ or NHPG$_0$)", and further, a peptide with protected N-terminal is indicated as "PG$_n$-AA$_{n'}$-AA$_{n'-1}$-...-AA$_1$-(OPG$_0$ or NHPG$_0$)".

The "C-protected amino acid" means an amino acid wherein the carboxyl group is protected and the amino group is not protected, and is indicated as "H-AA-OPG$_0$".

The "C-protected amino acid amide" means an amino acid amide wherein the amide group is protected and the amino group is not protected, and is indicated as "H-AA-NHPG$_0$".

The "N-protected amino acid" means an amino acid wherein the amino group is protected and the carboxy group is not protected, and this is indicated as shown by "PG$_n$-AA-OH".

The "N-protected amino acid amide" means amino acid amide wherein the amino group is protected and the amide group is not protected, and is indicated as "PG$_n$-AA-NH$_2$".

The "N-protected amino acid active ester" means an amino acid wherein the amino group is protected and the carboxy group is activated by E, and is indicated as "$PG_n$-AA-OE".

The "N-protected peptide active ester" means a peptide wherein the N-terminal amino group is protected and the C-terminal carboxy group is activated by E.

N-Protected amino acid active ester or N-protected peptide active ester that can be isolated is one wherein E is pentafluorophenyl, Su or Nb. Other N-protected amino acid active ester or N-protected peptide active ester is produced in the reaction system by reacting N-protected amino acid with a condensing agent (e.g., EDC) and an activator (e.g., HOBt).

The "N-Fmoc amino acid" means an amino acid wherein the amino group is protected by Fmoc and the carboxy group is not protected.

The "N-Fmoc amino acid amide" means an amino acid amide wherein the amino group is protected by Fmoc and the amide group is not protected.

The "N-Fmoc amino acid active ester" means an amino acid wherein the amino group is protected by Fmoc and the carboxy group is active-esterified by E.

The "N-Fmoc peptide active ester" means a peptide wherein the N-terminal amino group is protected by Fmoc and the C-terminal carboxy group is active-esterified by E.

N-Fmoc amino acid active ester or N-Fmoc peptide active ester that can be isolated is one wherein E is pentafluorophenyl, Su or Nb. Other N-Fmoc amino acid active ester or N-Fmoc peptide active ester is produced in the reaction system by reacting N-Fmoc amino acid with a condensing agent (e.g., EDC) and an activator (e.g., HOBt).

The "C-protected peptide" is a peptide wherein the C-terminal carboxy group or C-terminal amide group is protected, and the N-terminal amino group is not protected, and is indicated as "H-$AA_{n'}$-$AA_{n'-1}$- . . . -$AA_1$-($OPG_0$ or $NHPG_0$)" (n' is an integer of two or more).

The "N-protected-C-protected peptide" means a peptide wherein all of the N-terminal amino group, and the C-terminal carboxy group or the C-terminal amide group are protected, and is indicated as "$PG_n$-$AA_{n'}$-$AA_{n'-1}$- . . . -$AA_1$-($OPG_0$ or $NHPG_0$)" (n' is an integer of two or more).

The "N-Fmoc-C-protected peptide" means a peptide wherein the N-terminal amino group is protected by Fmoc, and the C-terminal carboxy group or C-terminal amide group is protected.

3. Method of Removing Fmoc Group

The method of removing the Fmoc group of the present invention includes a step of mixing compound (I) (that is, HS-L-COOH), an amino group-containing compound protected by an Fmoc group and a base to give a reaction mixture containing compound (II) (that is, Fm—S-L-COOH) and the amino group-containing compound, and a step of washing the obtained reaction mixture with a basic aqueous solution to remove compound (II) (in the aforementioned formulas, L is a $C_{1-8}$ alkylene group optionally having substituent(s), and Fm is a 9-fluorenylmethyl group).

The amino group-containing compound is not particularly limited as long as it is a compound having the primary amino group and/or the secondary amino group as mentioned above. Examples of the amino group-containing compound include peptide, amino acid, amino acid amide and the like. In the method of removing the Fmoc group of the present invention, only one kind of the amino group-containing compound protected by the Fmoc group may be used, or two or more kinds thereof may be used in combination.

When the amino group-containing compound is a low-molecular-weight compound having a free carboxy group, compound (II) as a byproduct, and the amino group-containing compound may be dissolved in a basic aqueous solution in the aforementioned step of washing with the basic aqueous solution, and the yield of the obtained amino group-containing compound may decrease. Therefore, the amino group-containing compound preferably does not have a free carboxy group. The amino group-containing compound protected by the Fmoc group is preferably N-Fmoc-C-protected peptide, N-Fmoc-C-protected peptide, N-Fmoc-C-protected amino acid or N-Fmoc-C-protected amino acid amide, which does not have a free carboxy group (sometimes to be abbreviated as "N-Fmoc-C-protected peptide etc." in the present specification). The amino group-containing compound obtained corresponding to the N-Fmoc-C-protected peptide and the like is preferably C-protected peptide, C-protected amino acid or C-protected amino acid amide (sometimes to be abbreviated as "C-protected peptide and the like" in the present specification).

The amino acid to be the base of the N-Fmoc-C-protected peptide and the like and C-protected peptide and the like, and the below-mentioned N-Fmoc amino acid, N-Fmoc amino acid active ester, N-Fmoc peptide and N-Fmoc peptide active ester may be any of natural amino acid and nonnatural amino acid. In addition, the amino acid may be any of an L form and a D form. Moreover, a mixture of racemic amino acids may also be used. Examples of the natural amino acid include Gly, Ala, Val, Leu, Ile, Ser, Thr, Asn, Gln, Asp, Glu, Lys, Arg, Cys, Met, Phe, Tyr, Trp, His, Pro, Orn, Sar, β-Ala, GABA and the like. Examples of the nonnatural amino acid include Dap and the like.

The N-Fmoc-C-protected peptide and the like and the C-protected peptide and the like may have a side chain functional group (amino group, carboxy group, sulfanyl group, hydroxy group, guanidyl group etc.). The side chain amino group may not be protected, but is preferably protected by a protecting group other than the Fmoc group (e.g., Boc, Z, Bsmoc, Alloc, Ac etc.). In addition, the side chain carboxy group is preferably protected by a protecting group like the C-terminal.

Examples of the carboxy-protecting group include alkyl having 1-6 carbon atoms such as Me, Et, tBu and the like, Bzl, p-nitrobenzyl, p-methoxybenzyl, Dpm, allyl, Bpr and the like. Examples of the amide-protecting group include Dmb, bis(4-methoxyphenyl)methyl and the like. In addition, the carboxy-protecting group and amide-protecting group preferably have a branched chain. Using a protecting group having a branched chain, the liposolubility of the N-Fmoc-C-protected peptide and the like and the C-protected peptide and the like can be improved, and a peptide having many amino acid residues is easily synthesized in the below-mentioned production method of peptide by the liquid phase synthesis method. Examples of the protecting group having a branched chain include Bzl(2,4-OPhy), Bzl(3,4,5-OPhy), Bzl(2-OBzl (3,4,5-OPhy)-4-OMe), Dpm(4,4'-OPhy) and the like.

Examples of the sulfanyl-protecting group include phenylcarbamoyl, Trt and the like. Examples of the hydroxyl-protecting group include Bzl, tBu and the like. Examples of the guanidyl-protecting group in the side chain include Pbf and the like.

L in the formula (I) shows a $C_{1-8}$ alkylene group optionally having substituent(s). Here, the "$C_{1-8}$" is the number of carbons contained in the alkylene group, and does not contain the number of carbons of the substituent that L has. When the number of carbons of the alkylene group is too large, the solubility of compound (II) as a byproduct in a basic aqueous solution decreases, and it cannot be removed sufficiently in the aforementioned washing step. Therefore, the number of carbons of the alkylene group is 8 or less, preferably 6 or less, more preferably 2 or less. Examples of the substituent that L can have include an alkyl group (e.g., Me, Et etc.), a carboxy group, an amino group and the like. Compound (I) is preferably at least one selected from the group consisting of 3-mercaptopropionic acid, thiomalic acid (also referred to as 2-mercaptosuccinic acid) and cysteine, more preferably 3-mercaptopropionic acid.

The amount of compound (I) to be used is preferably 1.0-30 mol, more preferably 3-10 mol, per 1 mol of the Fmoc group contained in the amino group-containing compound protected by the Fmoc group. When the amount of compound (I) to be used is too small, the Fmoc group cannot be sufficiently removed. On the other hand, when the amount is too large, removal of compound (I) itself becomes difficult. When the method of removing the Fmoc group of the present invention is utilized to a production method of peptide, impurity is sometimes produced easily due to the condensation reaction of peptide.

Compound (I), the amino group-containing compound protected by the Fmoc group and a base are generally reacted in a solvent. Examples of the solvent include chloroform, methylene chloride, CPME, DMF, NMP, ethyl acetate, acetonitrile, THF, a mixed solvent thereof and the like. The amount of the solvent to be used is generally 3- to 100-fold weight, preferably 5- to 30-fold weight, relative to the amino group-containing compound protected by the Fmoc group. While the reaction temperature varies depending on the amino group-containing compound protected by the Fmoc group, it is generally 0 to 50° C., preferably 10 to 30° C. The reaction time is generally 0.1-24 hr, preferably 1-5 hr.

Examples of the base to be used for the removal reaction of the Fmoc group include DBU, DABCO, $Et_3N$, $Na_2CO_3$, NaOtBu, KOtBu, $iPr_2EtN$ and the like. Only one kind of the base may be used, or two or more kinds thereof may be used in combination. The base is preferably an organic base, more preferably DBU. The amount of the base to be used is preferably 0.5-5 mol, more preferably 1-3 mol, per 1 mol of the carboxy group of compound (I) to be used. When the amount of the base to be used is too small, the reaction rate of the Fmoc group removal reaction is not sufficiently improved. On the other hand, when the amount is too large, removal of the base becomes difficult, and side reactions such as racemization of peptide and the like can occur when the method of removing the Fmoc group of the present invention is used for the production method of peptide.

One of the characteristics of the method of removing the Fmoc group of the present invention is removal of compound (II) as a byproduct by washing the reaction mixture obtained by the aforementioned reaction with a basic aqueous solution. Generally, washing means removal of a contaminant substance by dissolving same in a liquid. The washing in the present invention means removal of compound (II) by dissolving same in a basic aqueous solution. The washing with a basic aqueous solution is performed by, for example, mixing and stirring a solution containing the reaction mixture and a basic aqueous solution, partitioning the organic layer and the aqueous layer, and removing the aqueous layer. In addition, the washing with a basic aqueous solution can easily remove not only compound (II) as a byproduct but also the residual compound (I).

In the conventional method of removing an Fmoc group using amine and the like, the reaction solution needs to be washed with an acidic aqueous solution to remove amine. In this connection, when the reaction solution after removal of the Fmoc group is washed with an acidic aqueous solution in the peptide synthesis, the obtained peptide transfers to the acidic aqueous solution since peptide has an amino group, and the yield of the peptide problematically decreases. Moreover, removal of the aqueous layer is problematically difficult since a reaction solution containing peptide (that is, organic layer) shows poor separation property from an acidic aqueous solution (that is, aqueous layer). As compared to conventional methods wherein an Fmoc group is removed by washing with an acidic aqueous solution after using such amine, the method of removing the Fmoc group of the present invention including washing with a basic aqueous solution can avoid a decrease in the yield of the peptide, shows good separation of the organic layer and the aqueous layer.

The basic aqueous solution is preferably at least one aqueous solution selected from the group consisting of lithium carbonate, potassium carbonate, sodium carbonate, lithium hydrogen carbonate, potassium hydrogen carbonate, sodium hydrogen carbonate, lithium hydroxide, potassium hydroxide and sodium hydroxide, more preferably an aqueous sodium carbonate solution. The concentration of the base in the basic aqueous solution is preferably 1-20 wt %, more preferably 5-15 wt %. When the concentration of the base is too low, compound (II) cannot be removed sufficiently. On the other hand, when the concentration is too high, the base sometimes remains undissolved in water or a side reaction may occur.

A basic aqueous solution is added to the reaction mixture until the pH of the basic aqueous solution after mixing with the reaction mixture reaches preferably 7-14, more preferably 8-12. The washing temperature with a basic aqueous solution is preferably 0 to 50° C., more preferably 10 to 30° C. The washing with a basic aqueous solution may be repeated.

The basic aqueous solution may contain a polar solvent. This polar solvent is preferably at least one selected from the group consisting of DMF, acetonitrile, methanol, ethanol, THF and NMP, more preferably DMF. When a polar solvent is used, the content thereof in the basic aqueous solution is preferably 1-50% by volume, more preferably 5-30% by volume.

By concentrating a solution obtained by the method of removing the Fmoc group of the present invention, an amino group-containing compound wherein the Fmoc group has been removed can be isolated. Where necessary, the amino group-containing compound may be isolated as an acid addition salt (hydrochloride, toluenesulfonate, methanesulfonate, hydrobromide, trifluoroacetate etc.) by adding an acid (e.g., hydrochloric acid, toluenesulfonic acid, methanesulfonic acid, hydrobromic acid, trifluoroacetic acid etc.) to the solution. Furthermore, a solution of the obtained amino group-containing compound can be directly used as a starting material of the below-mentioned production method of peptide by the liquid phase synthesis method.

4. Production Method of Peptide by Liquid Phase Synthesis Method

When the amino group-containing compound protected by an Fmoc group is N-Fmoc-C-protected peptide and the like, and the corresponding amino group-containing compound obtained is C-protected peptide and the like, the method of removing the Fmoc group of the present invention can be preferably used for the production method of peptide by the liquid phase synthesis method (hereinafter sometimes to be abbreviated as "liquid phase peptide synthesis method"). The "liquid phase synthesis method" in the present invention means a synthesis method other than the solid phase synthesis method, which includes, in addition to a homogenous reaction wherein all reagents are dissolved in the solvent, a heterogeneous reaction wherein all or a part of the reagents is not dissolved in the solvent, but dispersed or suspended therein.

The liquid phase peptide synthesis method of the present invention including the aforementioned method of removing the Fmoc group is explained below.

While the peptide to be the final object product of the liquid phase peptide synthesis method of the present invention is not particularly limited, it preferably shows an amino acid residue number of about 2-40, which is generally seen in synthetic peptides. The peptide obtained by the liquid phase peptide synthesis method of the present invention can be utilized for, for example, synthetic pharmaceutical peptide, cosmetic, electronic material (organic EL and the like), food and the like.

One embodiment of the liquid phase peptide synthesis method of the present invention includes (1) a step of condensing C-protected peptide, C-protected amino acid or C-protected amino acid amide, and N-Fmoc amino acid or N-Fmoc peptide in the presence of a condensing agent (preferably condensing agent and activator) to give an N-Fmoc-C-protected peptide (hereinafter to be abbreviated as "coupling step (1)"), and/or (2) a step of condensing C-protected peptide, C-protected amino acid or C-protected amino acid amide, and N-Fmoc amino acid active ester or N-Fmoc peptide active ester to give an N-Fmoc-C-protected peptide (hereinafter to be abbreviated as "coupling step (2)".). For the liquid phase peptide synthesis method of the present invention, a general method conventionally used for the peptide synthesis chemistry can be employed without a particular limitation.

By repeating the aforementioned coupling steps (1) and/or (2), and then a step of removing the Fmoc group from the obtained N-Fmoc-C-protected peptide (hereinafter sometimes to be abbreviated as "N-terminal deprotection step"), C-protected peptide having a desired number of amino acid residues is obtained. Finally, a step of removing the C-terminal protecting group of the C-protected peptide, and a step of removing the protecting group of the side chain functional group where necessary (hereinafter sometimes to be abbreviated as the "final deprotection step") afford the final object product peptide.

One embodiment of the aforementioned liquid phase peptide synthesis method using the N-Fmoc amino acid or N-Fmoc amino acid active ester can be shown by the following scheme. In the following scheme, the nth peptide elongation reaction is indicated as "peptide elongation reaction (n)", and the coupling steps (1) and/or (2) constituting the peptide elongation reaction (n), and the N-terminal deprotection step thereafter are indicated as "coupling step (1-n)", "coupling step (2-n)" and "N-terminal deprotection step (n)", respectively. A liquid phase peptide synthesis method wherein the N-Fmoc amino acid or N-Fmoc amino acid active ester in the scheme below is replaced by N-Fmoc peptide or N-Fmoc peptide active ester, respectively, is also encompassed in the scope of the present invention.

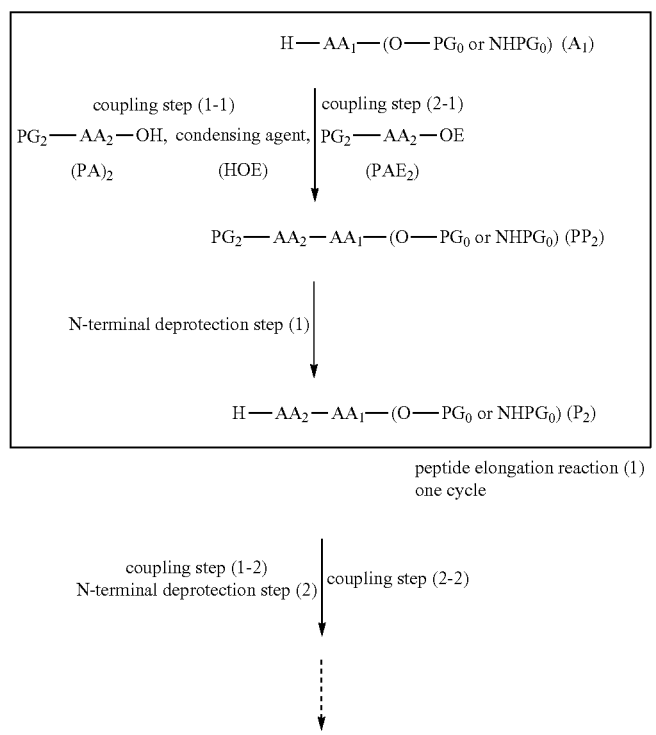

-continued

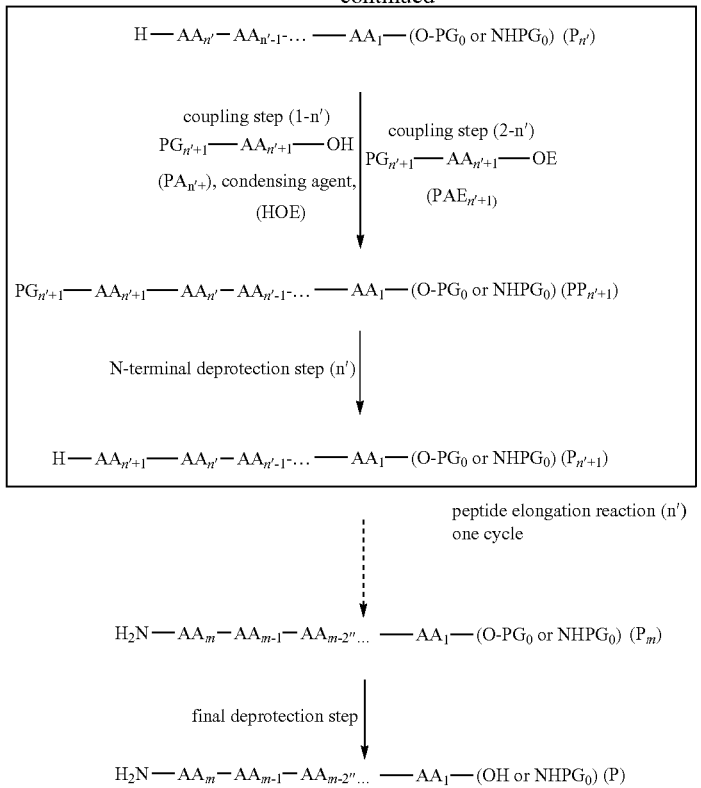

In the above-mentioned scheme, $A_1$ is C-protected amino acid or C-protected amino acid amide;

$PA_2$ and $PA_{n'+1}$ are each N-Fmoc amino acid;

$PAE_2$ and $PAE_{n'+1}$ are each N-Fmoc amino acid active ester;

$PP_2$ and $PP_{n'+1}$ are each N-Fmoc-C-protected peptide;

$P_2$, $P_{n'}$, $P_{n'+1}$ and $P_m$ are each C-protected peptide, subscripts 2, n', n'+1 and m are each the number of amino acid residues of the C-protected peptide, n' is an integer of two or more, m is an integer of not less than 3, and shows the number of amino acid residues of the final object product peptide; and P is the final object product peptide (number of amino acid residues m).

In the liquid phase peptide synthesis method of the present invention, the aforementioned removal method of the Fmoc group may be performed before the start of the elongation reaction (i.e., before the aforementioned coupling steps (1-1) and/or (2-2)) to prepare C-protected peptide, C-protected amino acid or C-protected amino acid amide to be used in these steps. In the liquid phase peptide synthesis method of the present invention, moreover, the aforementioned removal method of the Fmoc group may be performed as at least one (preferably all) of the N-terminal deprotection step to prepare a C-protected peptide.

Each step is sequentially explained in the following.

4-1. Coupling Step (1)

In coupling step (1), for example, an N-Fmoc-C-protected peptide wherein one amino acid residue has elongated is obtained by mixing C-protected peptide, C-protected amino acid or C-protected amino acid amide, and N-Fmoc amino acid, and a condensing agent (preferably a condensing agent and an activator) in a solvent. Using N-Fmoc peptide instead of N-Fmoc amino acid, moreover, an N-Fmoc-C-protected peptide wherein amino acid residues in the number of the amino acid residues of N-Fmoc peptide have elongated is obtained. The number of the amino acid residues of N-Fmoc peptide used here is preferably 2-20, more preferably 2-10.

While the order of addition of the components is not particularly limited, when the C-protected peptide is obtained by peptide elongation reaction (n−1) before this one, N-Fmoc amino acid or N-Fmoc peptide and a condensing agent (and preferably an activator) can be added to a solution of the C-protected peptide in a reaction vessel.

The amount of N-Fmoc amino acid or N-Fmoc peptide to be used is generally 0.9 to 4.0 equivalents, preferably 1.0 to 1.5 equivalents, relative to the C-protected peptide and the like. When the amount is smaller than this range, unreacted C-protected peptide and the like, tends to remain, and when the amount is larger, excess N-Fmoc amino acid or N-Fmoc peptide cannot be removed easily.

When C-protected peptide and the like is used as acid addition salt, a base is added for neutralization. Examples of the base include triethylamine, diisopropylethylamine, pyridine, N-methylmorpholine and the like. The amount of this base to be used is generally 0.5 to 2.0 equivalents, preferably 1.0 to 1.5 equivalents, relative to the C-protected peptide and the like. When the amount of the base to be used is smaller than this range, neutralization becomes insufficient and the reaction does not often proceed smoothly.

Examples of the condensing agent include EDC (including hydrochloride and free form), DIPC, DCC, BOP, PyBOP, PyBroP, HBTU, HCTU, TBTU, HATU, CDI, DMT-MM and the like can be mentioned. Of these, EDC is preferable from the aspects of residual condensing agent and decomposed condensing agent. The amount of the condensing agent to be used is generally 0.8 to 4.0 equivalents, preferably 1.0 to 1.5 equivalents, relative to N-Fmoc amino acid.

In coupling step (1), an activator is preferably added to promote the reaction and suppress side reactions such as racemization and the like. Here, the activator is a reagent that converts, in the presence of a condensing agent, amino acid to the corresponding active ester, symmetric anhydride and the like to facilitate formation of a peptide bond (amide bond). Examples of the activator include HOBt, HOCt, HOAt, HOOBt, HOSu, HOPht, HONb, pentafluorophenol and the like. Of these, HOBt, HOOBt, HOCt, HOAt, HONb, and HOSu are preferable. The amount of the activator to be used is generally 0 to 4.0 equivalents, preferably 0.1 to 1.5 equivalents, relative to N-Fmoc amino acid.

The solvent to be used in coupling step (1) is not particularly limited as long as it does not inhibit the reaction. Examples of the solvent include DMF, NMP, ethyl acetate, THF, acetonitrile, chloroform, methylene chloride, a mixed solvent thereof and the like. Of these, ethyl acetate and DMF are preferable. The amount of the solvent to be used is generally 3- to 100-fold weight, preferably 5- to 20-fold weight, relative to the C-protected peptide and the like.

The reaction temperature is generally within the range of −20° C. to 40° C., preferably 0° C. to 30° C. The reaction time is generally 0.5 to 30 hr.

Workup may be performed after completion of the reaction of coupling step (1). This workup is the same as that after completion of the reaction of coupling step (2), and will be explained altogether in "4-3. Workup of coupling steps (1) and (2)" after "4-2. Coupling step (2)".

4-2. Coupling Step (2)

In coupling step (2), for example, an N-Fmoc-C-protected peptide wherein one amino acid residue has elongated is obtained by mixing C-protected peptide, C-protected amino acid or C-protected amino acid amide, and N-Fmoc amino acid active ester in a solvent. Using N-Fmoc peptide active ester instead of N-Fmoc amino acid active ester, moreover, an N-Fmoc-C-protected peptide wherein amino acid residues in the number of the amino acid residues of N-Fmoc peptide active ester have elongated is obtained. The number of the amino acid residues of N-Fmoc peptide active ester used here is preferably 2-10, more preferably 2-5.

While the order of addition of the components is not particularly limited, when the C-protected peptide is obtained by peptide elongation reaction (n−1) before this one, N-Fmoc amino acid active ester or N-Fmoc peptide active ester can be added to a solution of the C-protected peptide in a reaction vessel.

The amount of N-Fmoc amino acid active ester or N-Fmoc peptide active ester to be used is the same as that of the N-Fmoc amino acid or N-Fmoc peptide in coupling step (1). The base, solvent and the amounts of use thereof in coupling step (2), the reaction temperature, reaction time and the like and other reaction conditions are also the same as those in coupling step (1). Workup may be performed after completion of the reaction of coupling step (2).

4-3. Workup of Coupling Steps (1) and (2)

After completion of the reactions of coupling steps (1) and (2), solid nucleophile removing reagents such as sulfanyl group-supported silica gel and the like (e.g., SH silica (manufactured by Fuji Silysia Chemical Ltd.) etc.) may be added, and the mixture is stirred and filtered to remove residues and byproducts in the reaction mixture that can be condensed with amine components, such as N-Fmoc amino acid activated ester, N-Fmoc peptide activated ester, isourea ester of N-Fmoc amino acid, symmetric anhydride of N-Fmoc amino acid and the like. In addition, activated ester may be deactivated in the washing step by washing with weak basic aqueous solution such as sodium carbonate and the like.

In the workup in coupling steps (1) and (2), washing with acidic aqueous solution and/or washing with basic aqueous solution is preferably performed. The washing with acidic aqueous solution can remove C-protected peptide, residual condensing agent and a decomposed product thereof, a base and the like into the aqueous layer. The washing with basic aqueous solution can remove additive, residual N-Fmoc amino acid and the like into the aqueous layer.

Washing with an acidic aqueous solution is performed, for example, by mixing and stirring the reaction mixture, a dilute aqueous hydrochloric acid solution (e.g., 1N aqueous hydrochloric acid solution), an aqueous solution of sulfuric acid, formic acid, citric acid, phosphoric acid and the like, partitioning the organic layer and the aqueous layer, and removing the aqueous layer.

Washing with a basic aqueous solution is performed, for example, by mixing and stirring the reaction mixture, an aqueous sodium hydrogen carbonate solution (e.g., 5 wt % aqueous sodium hydrogen carbonate solution), an aqueous sodium carbonate solution, an aqueous potassium carbonate solution and the like, partitioning the organic layer and the aqueous layer, and removing the aqueous layer.

Where necessary, washing with water may be further applied.

Particularly, when the above-mentioned (1) protecting group using the diphenylmethane compound described in WO 2010/113939A1 as a protecting reagent, (2) protecting group using the fluorene compound described in WO 2010/104169A1 as a protecting reagent, (3) protecting group using the benzyl compound described in WO 2011/078295A1 as a protecting reagent, (4) protecting group using the branched chain-containing aromatic compound described in WO 2012/029794A1 is used as a protecting group of the C-terminal carboxy group or amide group, impurities other than the object product can be efficiently removed into the aqueous layer side by washing with an acidic aqueous solution, washing with a basic aqueous solution and/or washing with water to be performed as necessary.

By concentrating the organic layer, N-Fmoc-C-protected peptide can be obtained. A solution of N-Fmoc-C-protected peptide without concentration or a concentrated solution thereof may be used for the N-terminal deprotection step thereafter.

4-4. N-Terminal Deprotection Step

In the liquid phase peptide synthesis method of the present invention, the aforementioned removal method of the Fmoc group may be performed to prepare C-protected peptide, C-protected amino acid or C-protected amino acid amide to be used when the elongation reaction is started, or may be performed as at least one (preferably all) of the N-terminal deprotection step. In the following, the Fmoc group removal method for the preparation of C-protected peptide, C-protected amino acid or C-protected amino acid amide to be used when the elongation reaction is started is explained in the N-terminal deprotection step.

When the removal method of the Fmoc group of the present invention is performed as an N-terminal deprotection step, compound (II) as a byproduct can be sufficiently removed. Therefore, the C-protected peptide, C-protected amino acid or C-protected amino acid amide obtained after the N-terminal deprotection step, which is in the form of a solution, can be used for the next step (i.e., coupling step (1) and/or (2), or final deprotection step) without isolation as a solid. A solution of the C-protected peptide and the like may be used for the next step after concentration as necessary.

As mentioned above, when the removal method of the Fmoc group of the present invention is performed as an N-terminal deprotection step, the obtained C-protected peptide and the like do not need to be isolated as a solid. Therefore, a peptide as the final object product can be produced by one-pot synthesis. Here, the one-pot synthesis means a synthesis method wherein, in the liquid phase peptide synthesis method, a peptide as the final object product is produced without taking the intermediate peptide obtained in each step (i.e., synthesis intermediate) from the reaction vessel.

In addition, when the removal method of the Fmoc group of the present invention is performed as an N-terminal deprotection step, N-Fmoc amino acid active ester, which is a byproduct of the coupling steps (1) and/or (2) and the like can be trapped by compound (I) and removed by washing thereafter with a basic aqueous solution. Therefore, the workup using sulfanyl group-supported silica gel and the like after the coupling steps (1) and/or (2) can be omitted.

4-5. Final Deprotection Step

In the final deprotection step, by removing the protecting group of the C-terminal of the C-protected peptide having the desired number of amino acid residues and, where necessary, the protecting group of the side chain functional group thereof, a peptide as the final object product can be obtained.

The method for removing the C-terminal protecting group and the side chain functional group is not particularly limited, and a deprotection method known per se can be used.

For example, when the protecting group is a lower alkyl group such as Me, Et and the like, it can be removed by reacting C-protected peptide with a base such as sodium hydroxide, potassium hydroxide and the like in a solvent such as water, aqueous organic solvent and the like at −20-40° C. for 0.5-10 hr.

When the protecting group is tBu, Pbf, Dmb, bis(4-methoxyphenyl)methyl and the like, it can be removed by reacting C-protected peptide with an acid such as trifluoroacetic acid, hydrochloric acid, methanesulfonic acid, tosylic acid, formic acid and the like in a solvent such as chloroform, methylene chloride, ethyl acetate, dioxane and the like at −20-40° C. for 0.5-10 hr.

When the protecting group is a Z group, it can be removed by a hydrogenation reaction of C-protected peptide using a catalyst such as palladium carbon and the like in a solvent such as methanol, DMF, acetic acid and the like at 0-40° C. for 0.5-100 hr, or by reacting C-protected peptide with a strong acid such as hydrogen fluoride, trifluoromethanesulfonic acid and the like at −20 to 40° C. for 0.5-10 hr.

When the protecting group is an Alloc group, it can be removed by a decomposition reaction of C-protected peptide using a homogeneous zero-valent palladium catalyst such as tetrakistriphenylphosphine palladium and the like. The amount of the homogeneous zero-valent palladium catalyst to be used is generally 0.01-1.0 equivalent, preferably 0.05-0.5 equivalent, relative to the protecting group to be removed.

The obtained peptide as the final object product can be isolated and purified by a method conventionally used in the peptide chemistry. For example, the final object product can be isolated and purified by extraction and washing, crystallization, chromatography and the like of the reaction mixture in the workup after the final deprotection step.

EXAMPLES

The present invention is explained in more detail in the following by referring to Examples, which are not to be construed as limitative. In the following, "%" showing the concentration means "wt %", unless specifically indicated.

Example 1

(i) Condensation of 3,4,5-Tri(2',3'-Dihydrophytyloxy)Benzyl Alcohol and N-Fmoc Amino Acid, and Subsequent Removal of Fmoc Group Using 3-Mercaptopropionic Acid 3,4,5-Tri(2',3'-dihydrophytyloxy)benzyl alcohol (2.0 g, 2.00 mmol) was dissolved in chloroform (20 ml), Fmoc-Leu-OH (779 mg, 2.20 mmol) was added, EDC.HCl (465 mg, 2.43 mmol) and DMAP (24 mg, 0.20 mmol) were added under ice-cooling, and the mixture was stirred at room temperature overnight. After completion of the reaction, the solvent was evaporated under reduced pressure, and the residue was dissolved in CPME (20 ml). To this solution were added 3-mercaptopropionic acid (0.87 mL, 10.02 mmol) and DBU (1.70 mL, 11.39 mmol) under ice-cooling, and the mixture was stirred at room temperature for 3 hr. After completion of the reaction, 1N hydrochloric acid/CPME (1.40 mL, 1.40 mmol), CPME (10 ml) and 20% brine (20 ml) were added under ice-cooling to give an organic layer and an aqueous layer. While stirring the mixture at room temperature, 10% aqueous sodium carbonate solution was added dropwise until the pH of the aqueous layer became 9.0, and the organic layer and the aqueous layer were partitioned (hereinafter this operation is sometimes to be abbreviated as "pH=9.0 washing"). The pH=9.0 washing was repeated one more time. The obtained organic layer was washed twice with 10% aqueous sodium carbonate solution (20 ml) and once with 20% brine (20 ml) with stirring at room temperature, and the organic layer and the aqueous layer were partitioned. The obtained organic layer was dried over sodium sulfate and filtered to give a CPME solution (30 ml) containing H-Leu-OBzl(3,4,5-OPhy). This CPME solution was directly used in the next step.

A small amount was sampled from the obtained CPME solution, and TOF-MS was measured. The measurement results and the measurement conditions thereof are described below. TOF-MS was measured in the same manner in the below-mentioned Example 1(ii) and the following.

TOF-MS: 1110.9 [MH$^+$]
measurement device: Waters LCT Premier XE
capillary voltage: 3000V
sample cone voltage: 86V
dissolution temperature: 350° C.
source temperature: 120° C.
injection volume: 2 μL (ii) Condensation of C-Protected Amino Acid and N-Fmoc Amino Acid, and Subsequent Removal of Fmoc Group Using 3-Mercaptopropionic Acid To the CPME solution (30 ml) of H-Leu-OBzl(3,4,5-OPhy) obtained in the above-mentioned Example 1(i) were added HOBt (81 mg, 0.60 mmol) and Fmoc-Tyr(tBu)-OH (1.01 g, 2.20 mmol), EDC.HCl (465 mg, 2.43 mmol) was added under ice-cooling, and the mixture was stirred at room temperature overnight. After completion of the reaction, the solvent was evaporated under reduced pressure until the mixture became 20 mL, to the concentrated solution were added under ice-cooling 3-mercaptopropionic acid (0.85 mL, 9.81 mmol) and DBU (1.66 mL, 11.18 mmol), and the mixture was stirred at room temperature for 3 hr. After completion of the reaction, to this solution were added under ice-cooling 1N hydrochloric acid/CPME (1.30 mL, 1.30 mmol), CPME (15 mL) and 20% brine (25 mL) to give an organic layer and an aqueous layer. Then, the aforementioned pH=9.0 washing was performed twice. The obtained organic layer was washed twice with 10% aqueous sodium carbonate solution and once with 20% brine with stirring at room temperature, and the organic layer and the aqueous layer were partitioned. The obtained organic layer was dried over sodium sulfate and filtered to give a CPME solution of H-Tyr(tBu)-Leu-OBzl (3,4,5-OPhy). This CPME solution was directly used in the next step.

TOF-MS: 1329.9[MH$^+$]

(III) Condensation of C-Protected Peptide and N-Fmoc Amino Acid or N-Fmoc Peptide, and Subsequent Removal of Fmoc Group Using 3-Mercaptopropionic Acid In the same manner as in the above-mentioned Example 1(ii), C-protected peptide obtained in the previous step and the following N-Fmoc amino acid or N-Fmoc peptide (indicated as "N-Fmoc amino acid etc." in the following Table 1) were condensed, and then the Fmoc group was removed, whereby the peptide chain was sequentially elongated.

TABLE 1

| peptide chain | N—Fmoc amino acid etc. | TOF-MS value [MH$^+$] | changes from Example 1 (ii) |
|---|---|---|---|
| 3rd residue | Fmoc-Glu(OtBu)—OH | 1514.9 | organic layer*[1] 40 mL |
| 4th residue | Fmoc-Glu(OtBu)—OH | 1700.0 | organic layer 40 mL |
| 5th residue | Fmoc-Pro-OH | 1797.1 | amount of DBU 2.1 mL (13.45 mmol) |
| 6th residue | Fmoc-Ile-OH | 1910.2 | — |
| 7th residue | Fmoc-Glu(OtBu)—OH | 2095.2 | organic layer 40 mL |
| 8th residue | Fmoc-Glu(OtBu)—OH | 2280.3 | organic layer 40 mL pH = 9.0 washed 3 times |
| 9th residue | Fmoc-Phe-OH | 2427.3 | organic layer 40 mL each washed twice*[2] |
| 10th residue | Fmoc-Asp(OtBu)—OH | 2598.3 | organic layer 50 mL each washed twice |
| 11th residue | Fmoc-Gly-OH | 2655.3 | organic layer 50 mL each washed twice |
| 12th residue | Fmoc-Asn(Trt)-OH | 3011.3 | organic layer 65 mL each washed twice |
| 13th and 14th residues | Fmoc-Gly-Gly-OH | 3125.2 | Amount of DBU 2.04 mL (13.67 mmol) organic layer 65 mL each washed twice |

*[1]organic layer: After completion of Fmoc group removal reaction, CPME was added to the reaction solution.
*[2]each washed twice: pH = 9.0 washing, after which washing with 10% aqueous sodium carbonate solution, and washing with 20% brine, each performed twice.

(iv) Condensation of C-Protected Peptide and N-Fmoc Amino Acid, and Subsequent Removal of Fmoc Group Using 3-Mercaptopropionic Acid To the CPME solution (65 mL) of H-Gly-Gly-Asn(Trt)-Gly-Asp(OtBu)-Phe-Glu(OtBu)-Glu(OtBu)-Ile-Pro-Glu(OtBu)-Glu(OtBu)-Tyr(tBu)-Leu-OBzl(3,4,5-OPhy) obtained in the above-mentioned Example 1(iii) were added HOBt (81 mg, 0.60 mmol), Fmoc-Gly-Gly-OH (765 mg, 2.16 mmol) and EDC.HCl (465 mg, 2.43 mmol), and the mixture was stirred at room temperature overnight. To this solution were added under ice-cooling 3-mercaptopropionic acid (0.85 mL, 9.81 mmol) and DBU (2.34 mL, 15.68 mmol), and the mixture was stirred at room temperature for 3 hr. After completion of the reaction, the reaction solution was neutralized with 1N hydrochloric acid/CPME (5 mL, 5.00 mmol), and the solvent was evaporated under reduced pressure. To the obtained residue was added 80% by volume aqueous acetonitrile solution (60 ml), and the precipitate was recovered by filtration. The recovered precipitate was slurry washed with acetonitrile (50 ml), then dried to give H-Gly-Gly-Gly-Gly-Asn(Trt)-Gly-Asp(OtBu)-Phe-Glu(OtBu)-Glu(OtBu)-Ile-Pro-Glu(OtBu)-Glu(OtBu)-Tyr(tBu)-Leu-OBzl (3,4,5-OPhy) (4.60 g, 1.42 mmol). The yield of the finally obtained C-protected peptide was calculated from 3,4,5-tri(2',3'-dihydrophytyloxy)benzyl alcohol (2.00 mmol), which is the starting material of Example 1(i), to find 71%.

TOF-MS: 3239.2[MH$^+$]

Example 2

(i) Condensation of 4,4'-(2',3'-Dihydrophytyloxy) Diphenylmethylamine and N-Fmoc Amino Acid, and Subsequent Removal of Fmoc Group Using 3-Mercaptopropionic Acid 4,4'-(2',3'-Dihydrophytyloxy)diphenylmethylamine (2.0 g, 2.38 mmol) was dissolved in chloroform (20 ml), HOBt (32 mg, 0.24 mmol) and Fmoc-Leu-OH (1.02 g, 2.89 mmol) were added, EDC.HCl (607 mg, 3.17 mmol) was added under ice-cooling, and the mixture was stirred at room temperature overnight. After completion of the reaction, the solvent was evaporated under reduced pressure, and the residue was dissolved in CPME (20 ml). To this solution were added under ice-cooling 3-mercaptopropionic acid (1.03 mL, 11.89 mmol) and DBU (2.02 mL, 13.55 mmol), and the mixture was stirred at room temperature for 3 hr. After completion of the reaction, to this solution were added under ice-cooling 1N hydrochloric acid/CPME (1.50 mL, 1.50 mmol), CPME (10 ml) and 20% brine (20 ml) to give an organic layer and an aqueous layer. Then, the aforementioned pH=9.0 washing was performed twice. The obtained organic layer was washed once with a mixed solvent of 10% aqueous sodium carbonate solution (20 ml) and DMF (4 mL), once with 10% aqueous sodium carbonate solution (20 ml) and twice with 20% brine (20 ml) with stirring at room temperature, and the organic layer and the aqueous layer were partitioned. The obtained organic layer was dried over sodium sulfate and filtered to give a CPME solution (30 ml) of H-Leu-NHDpm(4,4'-OPhy). This CPME solution was directly used in the next step.

TOF-MS: 889.6[MH$^+$]

(ii) Condensation of C-Protected Amino Acid Amide and N-Fmoc Amino Acid, and Subsequent Removal of Fmoc Group Using 3-Mercaptopropionic Acid To the CPME solution (30 ml) of H-Leu-NHDpm(4,4'-OPhy) were added HOBt (192 mg, 1.43 mmol) and Fmoc-Tyr(tBu)-OH (1.26 g, 2.74 mmol), EDC.HCl (607 mg, 3.17 mmol) was added under ice-cooling, and the mixture was stirred at room temperature overnight. After completion of the reaction, the solvent was evaporated under reduced pressure until the mixture became 25 mL, to the concentrated solution were added under ice-cooling 3-mercaptopropionic acid (1.03 mL, 11.89 mmol) and DBU (2.02 mL, 13.55 mmol), and the mixture was stirred at room temperature for 3 hr. After completion of the reaction, to this solution were added under ice-cooling 1N hydrochloric acid/CPME (1.50 mL, 1.50 mmol), CPME (5 mL) and 20% brine (25 mL) to give an organic layer and an aqueous layer. Then, the aforementioned pH=9.0 washing was performed twice. The obtained organic layer was washed twice with 10% aqueous sodium carbonate solution and twice with 20% brine with stirring, and the organic layer and the aqueous layer were partitioned. The obtained organic layer was dried over sodium sulfate and filtered to give a CPME solution of H-Tyr(tBu)-Leu-NHDpm(4,4'-OPhy). This CPME solution was directly used in the next step.

TOF-MS: 1108.7[MH$^+$]

(iii) Condensation of C-Protected Peptide and N-Fmoc Amino Acid, and Subsequent Removal of Fmoc Group Using 3-Mercaptopropionic Acid To the CPME solution (30 ml) of H-Tyr(tBu)-Leu-NHDpm(4,4'-OPhy) were added HOBt (96 mg, 0.71 mmol) and Fmoc-Glu(OtBu)-OH (1.11 g, 2.61 mmol), EDC.HCl (552 mg, 2.88 mmol) was added under ice-cooling, and the mixture was stirred at room temperature overnight. After completion of the reaction, the solvent was evaporated under reduced pressure until the mixture became 25 mL, to the concentrated solution were added under ice-cooling 3-mercaptopropionic acid (0.62 mL, 7.13 mmol) and DBU (1.60 mL, 10.70 mmol), and the mixture was stirred at room temperature for 3 hr. After completion of the reaction, to this solution were added under ice-cooling 1N hydrochloric acid/CPME (3.21 mL, 3.21 mmol), CPME (10 ml) and 20% brine (25 mL) to give an organic layer and an aqueous layer. Then, the aforementioned pH=9.0 washing was performed three times. The obtained organic layer was washed once with a mixed solvent of 10% aqueous sodium carbonate solution (25 mL) and DMF (5 mL), twice with 10% aqueous sodium carbonate solution (25 mL) and twice with 20% brine (25 mL) with stirring at room temperature, and the organic layer and the aqueous layer were partitioned. The obtained organic layer was dried over sodium sulfate and filtered to give a CPME solution of H-Glu(OtBu)-Tyr(tBu)-Leu-NHDpm(4,4'-OPhy). This CPME solution was directly used in the next step.

TOF-MS: 1293.8[MH$^+$]

(IV) Condensation of C-Protected Peptide and N-Fmoc Amino Acid, and Subsequent Removal of Fmoc Group Using 3-Mercaptopropionic Acid In the same manner as in the above-mentioned Example 2(iii), the C-protected peptide obtained in the previous step and the following N-Fmoc amino acid were condensed, and then the Fmoc group was removed, whereby the peptide chain was sequentially elongated.

TABLE 2

| peptide chain | N—Fmoc amino acid | TOF-MS value [MH$^+$] | changes from Example 2 (iii) |
|---|---|---|---|
| 4th residue | Fmoc-Glu(OtBu)—OH | 1478.8 | no washing with mixed solvent of 10% aqueous sodium carbonate solution and DMF |
| 5th residue | Fmoc-Pro-OH | 1575.9 | organic layer*[1] 40 mL no washing with mixed solvent of 10% aqueous sodium carbonate solution and DMF |
| 6th residue | Fmoc-Leu-OH | 1688.9 | — |
| 7th residue | Fmoc-Glu(OtBu)—OH | 1874.0 | organic layer 40 mL |
| 8th residue | Fmoc-Glu(OtBu)—OH | 2059.1 | organic layer 40 mL |

TABLE 2-continued

| peptide chain | N—Fmoc amino acid | TOF-MS value [MH$^+$] | changes from Example 2 (iii) |
|---|---|---|---|
| residue | Glu(OtBu)—OH | | amount of DBU 1.95 mL (13.08 mmol) |
| 9th residue | Fmoc-Lys(Boc)-OH | 2287.2 | organic layer 40 mL |
| 10th residue | Fmoc-Pro-OH | 2384.1 | organic layer 40 mL amount of DBU 1.95 mL (13.08 mmol) |
| 11th residue | Fmoc-Gly-OH | 2441.2 | organic layer 45 mL DMF 9 mL was added in 3rd pH = 9.0 washing |

*[1] organic layer: After completion of Fmoc group removal reaction, CPME was added to the reaction solution.

(v) Condensation of C-Protected Peptide and N-Fmoc Amino Acid, and Subsequent Removal of Fmoc Group Using 3-Mercaptopropionic Acid To the CPME solution (45 mL) of H-Gly-Pro-Lys(Boc)-Glu(OtBu)-Glu(OtBu)-Leu-Pro-Glu(OtBu)-Glu(OtBu)-Tyr(tBu)-Leu-NHDpm(4,4'-OPhy) obtained in the above-mentioned Example 2(iv) were added HOBt (192 mg, 1.43 mmol), Fmoc-Gly-Gly-OH (765 mg, 2.62 mmol) and EDC.HCl (552 mg, 2.88 mmol), and the mixture was stirred at room temperature overnight. After completion of the reaction, 3-mercaptopropionic acid (0.62 mL, 7.13 mmol) and DBU (1.78 mL, 11.89 mmol) were added under ice-cooling, and the mixture was stirred at room temperature for 3 hr. After completion of the reaction, the reaction solution was neutralized with 1N hydrochloric acid/CPME (4.28 mL, 4.28 mmol) and the solvent was evaporated under reduced pressure. To the obtained residue was added 80% by volume aqueous acetonitrile solution (70 ml), and the precipitate was recovered by filtration. The recovered precipitate was slurry washed with acetonitrile (50 ml), then dried to give H-Gly-Pro-Lys(Boc)-Glu(OtBu)-Glu(OtBu)-Leu-Pro-Glu(OtBu)-Glu(OtBu)-Tyr(tBu)-Leu-NHDpm(4,4'-OPhy) (4.40 g, 1.72 mmol). The yield of the finally obtained C-protected peptide was calculated from 4,4'-(2',3'-dihydrophytyloxy)diphenylmethylamine (2.38 mmol), which is the starting material of Example 2(i), to find 72%.

TOF-MS: 2555.1[MH$^+$]

Example 3

(i) Condensation of 2,4-Di(2',3'-Dihydrophytyloxy)Benzyl Alcohol and N-Fmoc Amino Acid, and Subsequent Removal of Fmoc Group Using 3-Mercaptopropionic Acid 2,4-Di(2',3'-dihydrophytyloxy)benzyl alcohol (2.0 g, 2.85 mmol) was dissolved in chloroform (20 ml), Fmoc-Gly-OH (1.12 g, 3.77 mmol) was added, EDC.HCl (794 mg, 4.14 mmol) and DMAP (42 mg, 0.34 mmol) were added under ice-cooling, and the mixture was stirred at room temperature overnight. After completion of the reaction, the solvent was evaporated under reduced pressure, and the residue was dissolved in CPME (20 ml). To this solution were added under ice-cooling 3-mercaptopropionic acid (0.74 mL, 8.56 mmol) and DBU (1.91 mL, 12.83 mmol), and the mixture was stirred at room temperature for 3 hr. After completion of the reaction, to this solution were added under ice-cooling 1N hydrochloric acid/CPME (3.85 mL, 3.85 mmol), CPME (15 mL) and 20% brine (25 mL) to give an organic layer and an aqueous layer. Then, the aforementioned pH=9.0 washing was performed twice. The obtained organic layer was washed once with a mixed solvent of 10% aqueous sodium carbonate solution (25 mL) and DMF (2.5 mL), twice with 10% aqueous sodium carbonate solution (25 mL) and three times with 20% brine (25 mL) with stirring, and the organic layer and the aqueous layer were partitioned. The obtained organic layer was dried over sodium sulfate and filtered to give a CPME solution (35 mL) of H-Gly-OBzl(2,4-OPhy). This CPME solution was directly used in the next step.

TOF-MS: 758.6[MH$^+$]

(ii) Condensation of C-Protected Amino Acid and N-Fmoc Amino Acid, and Subsequent Removal of Fmoc Group Using 3-Mercaptopropionic Acid To the CPME solution (35 mL) of H-Gly-OBzl(2,4-OPhy) were added HOBt (116 mg, 0.86 mmol) and Fmoc-Glu(OtBu)-OH (1.60 g, 3.76 mmol), EDC.HCl (794 mg, 4.14 mmol) was added under ice-cooling, and the mixture was stirred at room temperature overnight. After completion of the reaction, the solvent was evaporated under reduced pressure until the mixture became 20 mL, to the concentrated solution was added under ice-cooling DBU (1.02 mL, 6.84 mmol), and the mixture was stirred at room temperature for 3 hr. After completion of the reaction, to this solution were added under ice-cooling 1N hydrochloric acid/CPME (5.48 mL, 5.48 mmol), CPME (20 ml) and 20% brine (30 ml) to give an organic layer and an aqueous layer. Then, the aforementioned pH=9.0 washing was performed twice. The obtained organic layer was washed once with a mixed solvent of 10% aqueous sodium carbonate solution (30 ml) and DMF (3 mL), once with 10% aqueous sodium carbonate solution (30 ml) and twice with 20% brine (30 ml) with stirring at room temperature, and the organic layer and the aqueous layer were partitioned. The obtained organic layer was dried over sodium sulfate and filtered to give a CPME solution (40 ml) of H-Glu(OtBu)-Gly-OBzl(2,4-OPhy), which was directly transferred to the next step.

TOF-MS: 943.5[MH$^+$]

(iii) Condensation of C-Protected Peptide and N-Fmoc Amino Acid, and Subsequent Removal of Fmoc Group Using 3-Mercaptopropionic Acid To the CPME solution (40 mL) of H-Glu(OtBu)-Gly-OBzl (2,4-OPhy) were added HOBt (116 mg, 0.86 mmol) and Fmoc-Leu-OH (1.11 g, 3.14 mmol), EDC.HCl (662 mg, 3.45 mmol) was added under ice-cooling, and the mixture was stirred at room temperature overnight. After completion of the reaction, the solvent was evaporated under reduced pressure until the mixture became 25 mL, to the concentrated solution were added under ice-cooling 3-mercaptopropionic acid (0.74 mL, 8.56 mmol) and DBU (1.91 mL, 12.83 mmol), and the mixture was stirred at room temperature for 3 hr. After completion of the reaction, to this solution were added under ice-cooling 1N hydrochloric acid/CPME (3.85 mL, 3.85 mmol), CPME (15 mL) and 20% brine (25 mL) to give an organic layer and an aqueous layer. Then, the aforementioned pH=9.0 washing was performed three times. The obtained organic layer was washed once with a mixed solvent of 10% aqueous sodium carbonate solution (25 mL) and DMF (2.5 mL), twice with 10% aqueous sodium carbonate solution (25 mL) and three times with 20% brine (25 mL) with stirring at room temperature, and the organic layer and the aqueous layer were partitioned. The obtained organic layer was dried over sodium sulfate and filtered to give a CPME solution of H-Leu-Glu(OtBu)-Gly-OBzl(2,4-OPhy). This CPME solution was directly used in the next step.

TOF-MS: 1056.7 [MH$^+$]

(iv) Condensation of C-Protected Peptide and N-Fmoc Amino Acid, and Subsequent Removal of Fmoc Group Using 3-Mercaptopropionic Acid In the same manner as in the above-mentioned Example 3(iii), the C-protected peptide obtained in the previous step and the following N-Fmoc amino acid were condensed, and then the Fmoc group was removed, whereby the peptide chain was sequentially elongated.

TABLE 3

| peptide chain | N—Fmoc amino acid | TOF-MS value [MH$^+$] | changes from Example 3 (iii) |
|---|---|---|---|
| 4th residue | Fmoc-Tyr(tBu)—OH | 1275.7 | amount of HOBt 193 mg (1.43 mmol) |
| 5th residue | Fmoc-Ser(tBu)—OH | 1418.8 | amount of HOBt 193 mg (1.43 mmol) DMF 3 mL was added in 1st and 3rd pH = 9.0 washings |
| 6th residue | Fmoc-Ser(tBu)—OH | 1561.9 | amount of HOBt 193 mg (1.43 mmol) organic layer*[1] 50 mL DMF 3 mL was added in 3rd pH = 9.0 washing |
| 7th residue | Fmoc-Val-OH | 1660.92 | amount of DBU 2.12 mL (14.20 mmol) organic layer 50 mL DMF 3 mL was added in 1st pH = 9.0 washing |

*[1] organic layer: After completion of Fmoc group removal reaction, CPME was added to the reaction solution.

(v) Condensation of C-Protected Peptide and N-Fmoc Amino Acid, and Subsequent Removal of Fmoc Group Using 3-Mercaptopropionic Acid To the CPME solution (80 ml) of H-Val-Ser(tBu)-Ser(tBu)-Tyr(tBu)-Leu-Glu(OtBu)-Gly-OBzl (2,4-OPhy) obtained in the above-mentioned Example 3(iv) were added HOBt (193 mg, 1.43 mmol), Fmoc-Asp(OtBu)-OH (1.29 g, 3.14 mmol) and EDC.HCl (662 mg, 3.45 mmol), and the mixture was stirred at room temperature overnight. After completion of the reaction, 3-mercaptopropionic acid (0.74 mL, 8.56 mmol) and DBU (1.91 mL, 12.83 mmol) were added under ice-cooling, and the mixture was stirred at room temperature for 3 hr. After completion of the reaction, and the mixture was neutralized with a mixture of MsOH (0.25 mL, 3.85 mmol) and chloroform (2.5 mL) and the solvent was evaporated under reduced pressure. To the obtained residue was added 80% by volume of aqueous acetonitrile solution (60 ml), and the precipitate was recovered by filtration. The recovered precipitate was slurry washed with acetonitrile (50 ml), then dried to give H-Asp(OtBu)-Val-Ser(tBu)-Ser(tBu)-Tyr(tBu)-Leu-Glu(OtBu)-Gly-OBzl(2,4-OPhy) (3.62 g, 1.97 mmol). The yield of the finally obtained C-protected peptide was calculated from 2,4-di(2',3'-dihydrophytyloxy)benzyl alcohol (2.85 mmol), which is the starting material of Example 3(i), to find 69%.

TOF-MS: 1832.0[MH$^+$]

Example 4

(i) Condensation of 2-(3,4,5-Tri(2',3'-Dihydrophytyloxy)Benzyloxy)-4-Methoxybenzyl Alcohol and N-Fmoc Amino Acid, and Subsequent Removal of Fmoc Group Using 3-Mercaptopropionic Acid 2-(3,4,5-Tri(2',3'-dihydrophytyloxy)benzyloxy)-4-methoxybenzyl alcohol (2.0 g, 1.76 mmol) was dissolved in chloroform (25 mL), Fmoc-Ser(tBu)-OH (176 mg, 0.46 mmol), EDC.HCl (97 mg, 0.51 mmol) and DMAP (2.2 mg, 0.018 mmol) were added six times every 30 min under ice-cooling, and the mixture was stirred at room temperature overnight. After completion of the reaction, the solvent was evaporated under reduced pressure, and the residue was dissolved in CPME (20 ml). To this solution were added under ice-cooling 3-mercaptopropionic acid (0.46 mL, 5.27 mmol) and DBU (1.34 mL, 9.00 mmol), and the mixture was stirred at room temperature for 3 hr. After completion of the reaction, to this solution were added dropwise under ice-cooling a mixture of MsOH (0.22 mL, 3.33 mmol) and CPME (2.2 mL), and CPME (15 mL) and 20% brine (30 ml) were added to give an organic layer and an aqueous layer. Then, the aforementioned pH=9.0 washing was performed three times. The obtained organic layer was washed once with a mixed solvent of 10% aqueous sodium carbonate solution (30 ml) and DMF (3 mL), twice with 10% aqueous sodium carbonate solution (30 ml) and three times with 20% brine (30 ml) with stirring at room temperature, and the organic layer and the aqueous layer were partitioned. The obtained organic layer was dried over sodium sulfate and filtered to give a CPME solution (35 mL) of H-Ser(tBu)-OBzl(2-OBzl(3,4,5-OPhy)-4-OMe). This CPME solution was directly used in the next step.

TOF-MS: 1276.8[MH$^+$]

(ii) Condensation of C-Protected Amino Acid and N-Fmoc Amino Acid

To the CPME solution (35 mL) of H-Ser(tBu)-OBzl(2-OBzl(3,4,5-OPhy)-4-OMe) was added HOBt (71 mg, 0.43 mmol), Fmoc-Thr(tBu)-OH (1.00 g, 2.51 mmol), EDC.HCl (529 mg, 2.76 mmol) and DMF (10 ml) were added under ice-cooling, and the mixture was stirred at room temperature overnight. After completion of the reaction, to the reaction solution was added 20% brine (30 ml) to give an organic layer and an aqueous layer. While stirring the obtained organic layer and aqueous layer, 10% aqueous sodium carbonate solution was added dropwise until the pH of the aqueous layer became 6.0, and the organic layer and the aqueous layer were partitioned (hereinafter this operation is sometimes to be abbreviated as "pH=6.0 washing"). The pH-6.0 washing was further repeated twice. The solvent in the obtained organic layer was evaporated under reduced pressure, the residue was dissolved in cyclohexane (40 ml), and the mixture was washed four times with 80% by volume of aqueous acetonitrile solution (30 ml) with stirring, and the organic layer and the aqueous layer were partitioned. The obtained organic layer was dried over sodium sulfate and filtered. The solvent in the obtained filtrate was evaporated under reduced pressure to give Fmoc-Thr(tBu)-Ser(tBu)-OBzl (2-OBzl(3,4,5-OPhy)-4-OMe).

TOF-MS: 1655.9[MH$^+$]

(iii) Removal of Fmoc Group, and Subsequent Condensation of C-Protected Peptide and N-Fmoc Amino Acid Fmoc-Thr(tBu)-Ser(tBu)-OBzl(2-OBzl(3,4,5-OPhy)-4-OMe) was dissolved in CPME (25 mL). To this solution was added DBU (0.26 mL, 1.76 mmol) under ice-cooling, and the mixture was stirred at room temperature for 3 hr. Compound (I) was not used for the removal of the Fmoc group.

After completion of the reaction, to this solution were added under ice-cooling 1N hydrochloric acid/CPME (1.67 mL, 1.67 mmol), HOBt (237 mg, 1.76 mmol), Fmoc-Phe-OH (1.16 g, 2.98 mmol), EDC.HCl (629 mg, 3.28 mmol) and DMF (6 mL), and the mixture was stirred at room temperature overnight. After completion of the reaction, 20% brine (30 ml) was added to give an organic layer and an aqueous layer. Then, the aforementioned pH=6.0 washing was performed three times. The solvent in the obtained organic layer was evaporated under reduced pressure, the residue was dissolved in cyclohexane (40 ml), and the mixture was washed four times with 80% by volume of aqueous acetonitrile solution (30 ml) and once with 20% brine (30 ml) with stirring, and the organic layer and the aqueous layer were partitioned. The obtained organic layer was dried over sodium sulfate and filtered. The solvent in the obtained filtrate was evaporated under reduced pressure to give Fmoc-Phe-Thr(tBu)-Ser(tBu)-OBzl(2-OBzl(3,4,5-OPhy)-4-OMe).

TOF-MS: 1802.9[MH$^+$]

(iv) Removal of Fmoc Group, and Subsequent Condensation of C-Protected Peptide and N-Fmoc Amino Acid The total amount of Fmoc-Phe-Thr(tBu)-Ser(tBu)-OBzl (2-OBzl(3,4,5-OPhy)-4-OMe) obtained in Example 4(iii) was dissolved in CPME (25 mL). To this solution was added under ice-cooling DBU (0.26 mL, 1.76 mmol), and the mixture was stirred at room temperature for 3 hr. Compound (I) was not used for the removal of the Fmoc group.

After completion of the reaction, to this solution were added under ice-cooling 1N hydrochloric acid/CPME (1.67 mL, 1.67 mmol), HOBt (237 mg, 1.76 mmol), Fmoc-Thr(tBu)-OH (0.91 g, 2.29 mmol), EDC.HCl (629 mg, 3.28 mmol) and DMF (6 mL), and the mixture was stirred at room temperature overnight. After completion of the reaction, 20% brine (30 ml) was added to give an organic layer and an aqueous layer. Then, the aforementioned pH-6.0 washing was performed three times. The solvent in the obtained organic layer was evaporated under reduced pressure, the residue was dissolved in cyclohexane (40 ml), and the mixture was washed once with 20% brine (30 ml) with stirring, and the organic layer and the aqueous layer were partitioned. The obtained organic layer was dried over sodium sulfate and filtered. The solvent in the obtained filtrate was evaporated under reduced pressure to give Fmoc-Thr(tBu)-Phe-Thr(tBu)-Ser(tBu)-OBzl(2-OBzl(3,4,5-OPhy)-4-OMe).

TOF-MS: 1959.9[MH$^+$]

(v) Removal of Fmoc Group Using 3-Mercaptopropionic Acid, and Subsequent Condensation of C-Protected Peptide and N-Fmoc Amino Acid Fmoc-Thr(tBu)-Phe-Thr(tBu)-Ser(tBu)-OBzl (2-OBzl(3,4,5-OPhy)-4-OMe) obtained in Example 4(iv) was dissolved in CPME to give a CPME solution (30 ml). To this CPME solution were added under ice-cooling 3-mercaptopropionic acid (0.46 mL, 5.27 mmol) and DBU (1.18 mL, 7.90 mmol), and the mixture was stirred at room temperature for 3 hr. After completion of the reaction, to this solution was added under ice-cooling a mixture of MsOH (0.15 mL, 2.37 mmol) and CPME (1.5 mL), CPME (20 ml) and 20% brine (30 ml) to give an organic layer and an aqueous layer. Then, the aforementioned pH-9.0 washing was performed twice. The obtained organic layer was washed three times with 10% aqueous sodium carbonate solution and three times with 20% brine with stirring at room temperature, and the organic layer and the aqueous layer were partitioned. The obtained organic layer was dried over sodium sulfate and filtered to give a CPME solution of H-Thr(tBu)-Phe-Thr(tBu)-Ser(tBu)-OBzl (2-OBzl (3,4,5-OPhy)-4-OMe). To this CPME solution were added under ice-cooling HOBt (71 mg, 0.53 mmol), Fmoc-Lys(Boc)-OH (994 mg, 2.12 mmol) and EDC.HCl (402 mg, 2.01 mmol), and the mixture was stirred at room temperature overnight. After completion of the reaction, the solvent in the reaction solution was evaporated under reduced pressure, 80% by volume of aqueous acetonitrile solution (40 ml) was added, and the precipitate was recovered by filtration. The recovered precipitate was dried to give Fmoc-Lys(Boc)-Thr(tBu)-Phe-Thr(tBu)-Ser(tBu)-OBzl(2-OBzl(3,4,5-OPhy)-4-OMe) (3.56 g, 1.63 mmol). The yield of the finally obtained N-Fmoc-C-protected peptide was calculated from 2-(3,4,5-tri(2',3'-dihydrophytyloxy)benzyloxy)-4-methoxybenzyl alcohol (1.76 mmol), which is the starting material of Example 4(i), to find 93%.

TOF-MS: 2188.1[MH$^+$]

Example 5

(i) Condensation of C-Protected Amino Acid Salt and N-Fmoc Amino Acid, and Subsequent Removal of Fmoc Group Using Thiomalic Acid H-Leu-OBzl-TsOH salt (394 mg, 1.00 mmol) was dissolved in chloroform (10 ml), triethylamine (0.14 mL, 1.00 mmol), HOBt (14 mg, 0.10 mmol) and Fmoc-Tyr(tBu)-OH (506 mg, 1.10 mmol) were added, EDC.HCl (232 mg, 1.21 mmol) was added under ice-cooling, and the mixture was stirred at room temperature overnight. After completion of the reaction, to this solution were added under ice-cooling thiomalic acid (450 mg, 3.00 mmol) and DBU (1.49 mL, 10.00 mmol), and the mixture was stirred at room temperature for 3 hr. After completion of the reaction, to this solution was added dropwise under ice-cooling a mixture of MsOH (0.23 mL, 3.60 mmol) and chloroform (2.3 mL), chloroform (10 ml) and 20% brine (20 ml) were added to give an organic layer and an aqueous layer. Then, the aforementioned pH=9.0 washing was performed three times. The obtained organic layer was washed three times with 10% aqueous sodium carbonate solution (20 ml) and three times with 20% brine (20 ml) with stirring at room temperature, and the organic layer and the aqueous layer were partitioned. The obtained organic layer was dried over sodium sulfate and filtered to give a chloroform solution (20 ml) of H-Tyr(tBu)-Leu-OBzl. This chloroform solution was directly used in the next step.

TOF-MS: 441.2[MH$^+$]

(ii) Condensation of C-Protected Amino Acid and N-Fmoc Amino Acid, and Subsequent Removal of Fmoc Group Using Thiomalic Acid To the chloroform solution (20 ml) of H-Tyr(tBu)-Leu-OBzl was added HOBt (41 mg, 0.30 mmol), Fmoc-Glu(OtBu)-OH (468 mg, 1.10 mmol) and EDC.HCl (232 mg, 1.21 mmol) were added under ice-cooling, and the mixture was stirred at room temperature overnight. After completion of the reaction, to this solution were added under ice-cooling thiomalic acid (450 mg, 3.00 mmol) and DBU (1.49 mL, 10.00 mmol), and the mixture was stirred at room temperature for 3 hr. After completion of the reaction, to this solution was added dropwise under ice-cooling a mixture of MsOH (0.23 mL, 3.60 mmol) and chloroform (2.3 mL), chloroform (10 ml) and 20% brine (20 ml) were added to give an organic layer and an aqueous layer. Then, the aforementioned pH=9.0 washing was performed three times. The obtained organic layer was washed three times with 10% aqueous sodium carbonate solution (20 ml) and twice with 20% brine (20 ml) with stirring at room temperature, and the organic layer and the aqueous layer were partitioned. The obtained organic layer was dried over sodium sulfate and filtered to give a chloroform solution (30 ml) of H-Glu(OtBu)-Tyr(tBu)-Leu-OBzl. This chloroform solution was directly used in the next step.

TOF-MS: 626.2[MH$^+$]

(iii) Condensation of C-Protected Peptide and N-Fmoc Amino Acid, and Subsequent Removal of Fmoc Group Using Thiomalic Acid To the chloroform solution (30 ml) of H-Glu(OtBu)-Tyr(tBu)-Leu-OBzl was added HOBt (68 mg, 0.50 mmol), Fmoc-Glu(OtBu)-OH (468 mg, 1.10 mmol) and EDC.HCl (232 mg, 1.21 mmol) were added under ice-cooling, and the mixture was stirred at room temperature overnight. After completion of the reaction, the solvent was evaporated under reduced pressure until the mixture became 15 mL, to the concentrated solution were added under ice-cooling thiomalic acid (450 mg, 3.00 mmol) and DBU (1.34 mL, 9.00 mmol), and the mixture was stirred at room temperature for 3 hr. After completion of the reaction, to this solution was added dropwise under ice-cooling a mixture of MsOH (0.17 mL, 2.70 mmol) and chloroform (1.7 mL), chloroform (15 mL) and 20% brine (30 ml) was added to give an organic layer and an aqueous layer. Then, the aforementioned pH=9.0 washing was performed three times. The obtained organic layer was washed three times with 10% aqueous sodium carbonate solution (30 ml) and twice with 20% brine (30 ml) with stirring at room temperature, and the organic layer and the aqueous layer were partitioned. The obtained organic layer was dried over sodium sulfate and filtered. The filtrate was recovered, and the solvent in the recovered filtrate was evaporated under reduced pressure. To the obtained residue was added hexane (10 ml), and the precipitate was recovered by filtration. The recovered precipitate was dried to give H-Glu(OtBu)-Glu(OtBu)-Tyr(tBu)-Leu-OBzl (787 mg, 0.97 mmol). The yield of the finally obtained C-protected peptide was calculated from H-Leu-OBzl.TsOH salt (1.00 mmol), which is the starting material of Example 5(i), to find 97%.

TOF-MS: 811.2[MH$^+$]

Example 6

Removal of Fmoc Group Using Thiomalic Acid

Fmoc-Leu-OBzl(3,4,5-OPhy) (0.075 mmol) was dissolved in chloroform (1 mL), thiomalic acid (33.8 mg, 0.23 mmol) and DBU (0.09 mL, 0.60 mmol) were added under ice-cooling, and the mixture was stirred at room temperature for 4 hr. The production rate of compound (II)(i.e., DBF-thiomalic acid adduct) on completion of the reaction was 91%. The production rate of compound (II) was calculated by quantitative analysis of DBF by HPLC using synthesized DBF as a standard product, calculating the production rate of DBF and then calculating the production rate of compound 2 (100-production rate of DBF). The calculation method of the following production rates is the same.

HPLC conditions are as described below.
measurement device: Waters AQUITY UPLC BEH C18 50 mm×2.1 mm I.D., 1.7 μm
measurement temperature: 40° C.
flow rate: 0.4 mL/min
injection volume: 2 μL
measurement wavelength: 220 nm
mobile phase A: 0.05% by volume aqueous trifluoroacetic acid solution
mobile phase B: 0.05% by volume trifluoroacetic acid acetonitrile solution
gradient time program: the concentration of mobile phase B was linearly increased from 20% by volume to 90% by volume in 10 min.

After completion of the reaction, to this solution were added under ice-cooling 1N hydrochloric acid/CPME (0.05 mL, 0.05 mmol), chloroform (5 mL) and 20% brine (5 mL) and, while stirring the mixture at room temperature, 10% aqueous sodium carbonate solution was added dropwise until the pH of the mixture became 9.0, and the organic layer and the aqueous layer m were partitioned. The obtained organic layer was washed three times with 10% aqueous sodium carbonate solution (20 ml) at room temperature, and the organic layer and the aqueous layer were partitioned. The absence of compound (II) in the organic layer (i.e., compound (II) was entirely removed into the aqueous layer) was confirmed by HPLC.

Example 7

Removal of Fmoc Group Using Cysteine

Fmoc-Leu-OBzl(3,4,5-OPhy) (0.075 mmol) was dissolved in chloroform (1 cysteine (27 mg, 0.23 mmol) and DBU (0.022 mL, 0.15 mmol) were added under ice-cooling, and the mixture was stirred at room temperature for 3 hr. The production rate of compound (II) (i.e., DBF-cysteine adduct) on completion of the reaction was 95%. After completion of the reaction, the reaction solution was concentrated, to the concentrated reaction solution was added CPME (5 mL), and the reaction solution was washed three times with 10% aqueous sodium carbonate solution (5 mL) at room temperature to remove compound (II).

Comparative Example 1

Removal of Fmoc Group Using Thiosalicylic Acid

Fmoc-Leu-OBzl(3,4,5-OPhy) (0.075 mmol) was dissolved in CPME (1 ml), thiosalicylic acid (35 mg, 0.23 mmol) and DBU (0.041 mL, 0.28 mmol) were added under ice-cooling, and the mixture was stirred at room temperature for 3.5 hr. The production rate of DBF-thiosalicylic acid adduct on completion of the reaction was 21%.

INDUSTRIAL APPLICABILITY

The removal method of the Fmoc group of the present invention can be utilized for industrial production of peptide and the like.

Although the present invention have been presented or described by referring to preferred embodiments of this invention, it will, however, be understood by those of ordinary skill in the art that various modifications may be made to the forms and details without departing from the scope of the invention as set forth in the appended claims. All patents, patent publications and other publications indicated or cited in the Specification are hereby incorporated in their entireties by reference.

The invention claimed is:
1. A method of removing an Fmoc group, comprising:
mixing an amino group-containing compound protected by an Fmoc group, a base, and a compound represented by formula (I):

HS-L-COOH             (I)

where L is a $C_{1-8}$ alkylene group optionally having at least one substituent, to obtain a reaction mixture comprising an amino group-containing compound and a compound represented by formula (II):

Fm—S-L-COOH             (II)

where Fm is a 9-fluorenylmethyl group; and
washing the reaction mixture with a basic aqueous solution such that the compound represented by the formula (II) is removed;
wherein the amino group-containing compound protected by an Fmoc group, and the amino group-containing compound, do not have a free carboxy group.

2. The method according to claim 1, wherein the base is an organic base.

3. The method according to claim 2, wherein the organic base is 1,8-diazabicyclo[5.4.0]-7-undecene.

4. The method according to claim 1, wherein the compound represented by the formula (I) is at least one selected from the group consisting of 3-mercaptopropionic acid, thiomalic acid and cysteine.

5. The method according to claim 1, wherein the basic aqueous solution is an aqueous solution of at least one selected from the group consisting of lithium carbonate, potassium carbonate, sodium carbonate, lithium hydrogen carbonate, potassium hydrogen carbonate, sodium hydrogen carbonate, lithium hydroxide, potassium hydroxide and sodium hydroxide.

6. The method according to claim 1, wherein the amino group-containing compound protected by an Fmoc group is N-Fmoc-C-protected peptide, N-Fmoc-C-protected amino acid or N-Fmoc-C-protected amino acid amide, and
the amino group-containing compound in the reaction mixture is C-protected peptide, C-protected amino acid or C-protected amino acid amide.

7. A method of producing a peptide by a liquid phase synthesis method, comprising:
removing an Fmoc group by the method according to claim 6.

8. The method according to claim 7, further comprising:
condensing C-protected peptide, C-protected amino acid or C-protected amino acid amide, and N-Fmoc amino acid or N-Fmoc peptide in the presence of a condensing agent to obtain the N-Fmoc-C-protected peptide.

9. The method according to claim 8, wherein the condensing is performed in the presence of an activator and the condensing agent.

10. The method according to claim 8, wherein the C-protected peptide, C-protected amino acid or C-protected amino acid amide is obtained by removing the Fmoc group, and subjected to the condensing without isolating as a solid.

11. The method according to claim 10, wherein the peptide is produced by one-pot synthesis.

12. The method according to claim 7, further comprising:
condensing C-protected peptide, C-protected amino acid or C-protected amino acid amide, and N-Fmoc amino acid active ester or N-Fmoc peptide active ester to obtain the N-Fmoc-C-protected peptide.

13. The method according to claim 12, wherein the C-protected peptide, C-protected amino acid or C-protected amino acid amide is obtained by removing the Fmoc group, and subjected to the condensing without isolating as a solid.

14. The method according to claim 13, wherein the peptide is produced by one-pot synthesis.

15. The method according to claim 7, further comprising:
(1) condensing C-protected peptide, C-protected amino acid or C-protected amino acid amide, and N-Fmoc amino acid or N-Fmoc peptide in the presence of a condensing agent; and
(2) condensing C-protected peptide, C-protected amino acid or C-protected amino acid amide, and N-Fmoc amino acid active ester or N-Fmoc peptide active ester to obtain the N-Fmoc-C-protected peptide.

16. The method according to claim 15, wherein the (1) condensing is performed in the presence of an activator and the condensing agent.

17. The method according to claim 15, wherein the C-protected peptide, C-protected amino acid or C-protected amino acid amide is obtained by removing the Fmoc group, and subjected to the (1) condensing and the (2) condensing without isolating as a solid.

18. The method according to claim 17, wherein the peptide is produced by one-pot synthesis.

* * * * *